United States Patent [19]
Toth et al.

[11] Patent Number: 5,882,645
[45] Date of Patent: Mar. 16, 1999

[54] PEPTIDE COMPOUNDS

[75] Inventors: Istvan Toth, Middlesex; William Anthony Gibbons, Kennington, both of United Kingdom

[73] Assignee: The School of Pharmacy, University of London, United Kingdom

[21] Appl. No.: 374,560

[22] PCT Filed: Jul. 23, 1993

[86] PCT No.: PCT/GB93/01558

§ 371 Date: Mar. 13, 1995

§ 102(e) Date: Mar. 13, 1995

[87] PCT Pub. No.: WO94/02506

PCT Pub. Date: Feb. 3, 1994

[30] Foreign Application Priority Data

Jul. 24, 1992 [GB] United Kingdom ............... 9215780

[51] Int. Cl.$^6$ .................... A61K 39/385; A61K 38/00
[52] U.S. Cl. ................... 424/194.1; 424/278.1; 530/334; 530/345
[58] Field of Search ............ 424/194.1, 193.1, 424/278.1; 530/345, 334

[56] References Cited

U.S. PATENT DOCUMENTS

| | | | |
|---|---|---|---|
| 3,326,682 | 6/1967 | Endermann et al. | 96/23 |
| 5,114,713 | 5/1992 | Sinigaglia | 424/88 |

FOREIGN PATENT DOCUMENTS

89/10348  11/1989  WIPO .

OTHER PUBLICATIONS

Muranishi S. et al. "Lipophilic peptides: Synthesis of laurol thyrotropin–releasing hormone and its biological activity" Pharm. Res. 1991, vol. 8, No. 5, pp. 649–652.
Nardelli B. et al. "Design of a complete synthetic peptide-based AIDS vaccine with a built–in adjuvant" Aids Research and Human Retroviruses. 1992, vol. 8, No. 8, pp. 14051407.
Hopp T.P. "Immunogenicity of a synthetic HBsAg peptide:Enhancement by conjugation to a fatty acid carrier" Mol. Immunol. 1984, vol. 21, No. 1, pp. 13–16.
Tam, J.P., "Synthetic Peptide Vaccine Design: Synthesis and Properties of a High–Density Multiple . . . ", Proc. Natl. Acad. Sci. USA, vol. 85, Aug. 1988, pp. 5409–5413.
Tam, J.P., et al., "Mechanisms for the Removal of Benzyl Protecting Groups in Synthetic Peptides by Trifluoromethanelsulfonic Acid–Trifluoroacetic Acid–Dimethyl Sulfide", J. Am. Chem. Soc., 1986, vol. 108, pp. 5242–5251.
Mitchell, A.R., et al., "A New Synthetic Route to tert–Butyloxycarbonylaminoacyl–4–(oxymethyl)phenylacetamidomethyl–resin, an Improved Support for Solid–Phase Peptide Synthesis", J. Org. Chem., vol. 43, No. 14, 1978, pp. 2845–2852.

Neckameyer, W.S., et al., "Nucleotide Sequence of Avian Sarcoma Virus UR2 and Comparison of Its Transforming Gene With Other Members of the Tyrosine Protein Kinase Oncogene Family", Journal of Virology, Mar. 1985, pp. 879–884.
Gibbons, W.A., et al., "Synthesis, Resolution and Structural Elucidation of Lipidic Amino Acids and Their Homo– and Hetero–Oligomers", Liebigs Ann. Chem., 1990, pp. 1175–1183.
Huang, W., et al., "Synthetic Vaccine Memetic", Rockefeller University, pp. 847–848. 12 Peptide Symposium. 1991.
Merrifield, R.B., "Solid Phase Peptide Synthesis. I. The Synthesis of a Tetrapeptide", Rockefeller Institute, Jul. 20, 1963, vol. 85, pp. 2149–2154.
Toth, I., et al., "Lipidic Peptides X$^1$. Synthesis, Structural and Physico–Chemical Elucidation of Lipidic Amino Acid Conjugates With Hydrophilic Compounds", Tetrahedron, vol. 48, No. 5, 1992, pp. 923–930.
Defoort, J–P., et al., "Complete Synthetic Vaccine With Built–In Adjuvant", Rockefeller University, pp. 845–846. Chem. Biol., Proc. Am Pept. Symp. 12th (1991).
DiMarchi, R., et al., "Protection of Cattle Against Foot–and–Mouth Disease by a Synthetic Peptide", Science, vol. 232, May 2, 1986, pp. 639–641.
Toth, I., et al., "Lipidic Amino Acid Based Synthetic Peptide Vaccine Adjuvant", Immunological Satellite Meeting, Budapest, Aug. 29–31, 1992 Abstract Only.
Toth, I., et al., "A Combined Adjuvant and Carrier System for Enhancing Synthetic Peptides Immunogenicity Utilising Lipidic Amino Acids", Tetrahedron Letters, vol. 34, No. 24, 1993, pp. 3925–3928.
Defoort, J–P., et al., "Macromolecular Assemblage in the Design of a Synthetic AIDS Vaccine", Proc. Natl. Acad. Sci. USA, vol. 89, May 1992, pp. 3879–3883.

*Primary Examiner*—James C. Housel
*Assistant Examiner*—Rosemary Ashton
*Attorney, Agent, or Firm*—Ostrolenk, Faber, Gerb & Soffen, LLP

[57] ABSTRACT

Synthetic peptides are widely used to generate antibodies. To induce high antibody response, it is known to conjugate the peptide to a carrier protein (e.g. KLH, BSA) or to incorporate it into polylysine to form a multiple antigenic peptide. Anchors may be built in which are based on fatty acids. According to the invention there is provided a novel lipidic amino acid based anchor system which can maximally enhance the antigenicity of a short synthetic peptide. These novel compounds are entirely peptide-based and may therefore be produced automatically by some step wise peptide synthesis, preferably solid phase step wise peptide synthesis. According to the invention there is also provided such a process.

16 Claims, 5 Drawing Sheets

PEPTIDE COMPOUNDS

The present invention relates to peptide compounds which comprise a lipophilic anchor section formed from at least one fatty amino acid moiety and a matrix core section having at least four amino acid functionalities which are the same and are selected from —$NH_2$, —COOH, —SH, —OH and derivatives thereof. Pharmaceutically active moieties, especially peptide antigens, can be bound to the amino acid functionalities for use as, for instance, vaccines and diagnostic agents. The lipophilic anchor allows the compound to be incorporated into lipid vesicles and/or cell membranes. The invention includes a process for producing the new compound by conventional peptide synthesis, usually on a solid matrix.

It is well recognised that synthetic peptides can induce antibodies reactive with their cognate sequences in the native proteins, that is the synthetic peptide and native protein comprise the same epitope. Specific antibodies are useful as reagents in various investigations. Furthermore peptide antigens, made by available peptide synthesis techniques, are useful for producing immunogens and for immunoprophylaxis and in affinity purification of proteins, antibodies, or other molecules.

Small peptide molecules may not be of sufficient molecular weight themselves to be immunogenic at all or to a sufficient degree, but can be rendered immunogenic or more immunogenic by conjugation to a carrier molecule, for instance to a protein or a synthetic polymer. The use of proteins, for instance bovine serum albumin (BSA), has been described. Although the conjugated product is antigenic, it comprises a large number of epitopes other than that associated with the synthetic peptide of interest. Di Marchi et al in Science (1986) 232, 639–641 describe a synthetic peptide comprising two immunologically significant regions of a virus coat protein joined by a spacer which has adequate molecular weight to induce an immune response. Again the spacer region can act as an epitope, which is undesirable.

James P Tam, in Proc. Natl. Acad. Sci. USA (1988) 85, 5409–5413, describes a new approach to increasing the molecular weight of synthetic peptide antigens called the multiple antigen peptide system (MAP). The MAP comprises a core matrix formed of a low number (n) of sequential levels of dendritically joined trifunctional amino acids, in practice lysine molecules. The core matrix has $2^n$ terminal functionalities, in practice amine functionalities, each of which can be conjugated with a synthetic peptide. The MAP was synthesized by forming the core matrix using conventional step wise solid phase procedure by contacting an excess of symmetrical anhydride of $N^\alpha$, $N^\epsilon$-Boc-Lys(Boc) with (Boc)-β-Ala-$OCH_2$-Pam resin (phenyl-acetamido methyl resin). Subsequent levels of the core were formed by similar steps. To each terminal amine functionality, a preformed synthetic peptide antigen molecule was joined via triglycyl linker, followed by cleavage from the resin by known means. In a MAP in which the matrix core comprises three levels of lysine and thus $2^3$ amine groups, there will be 8 peptide groups per molecule, and where the peptide antigen groups each have a molecular weight of say 1200 the peptide antigen accounts for more than 80% of the total weight of the MAP. The MAP was antigenic, raising antibodies reactive with native proteins including the same peptide sequence (p60$_{src}$)

4-branch and 8-branch versions of F-moc protected dendritically-linked poly-lysine cores attached to peptide synthesis resins via a β-alanine residue are commercially available from Applied Biosystems, Inc.

At the 12th American Peptide Symposium in Boston in 1991, Defoort et al, describe a MAP with a preformed lipid anchor conjugated to it to allow incorporation into liposomes. The lipid anchor comprises a total of 3 hydrophobic chains per molecule. The lipid tails comprise fatty acids (palmitoyl groups) joined by esterification reactions to the two free hydroxyl groups of glycerol, acting as a polyhydroxy linker compound, which is in turn joined to the MAP core by reaction of the third hydroxy group with the thiol group of cysteine to form a thioether link, the cysteine being joined via its carboxylic acid group to the side chain amine group of a lysine residue and having a third palmitoyl group attached to the amine functionality of the cysteine residue.

The lysine residue is then joined via a linker of two serine residues to the dendritic poly(lysine) core. The peptide antigen (4 chains per molecule) was joined to the four amine functionalities of the core.

A problem with the Defoort et al proposals is that the compound is complicated to make, as it requires chemical reactions other than peptide synthesis steps, to produce the ester linkages of palmitoyl groups to the glyceryl hydroxyl groups and the thioether link between cysteine and glycerol.

Although the lipid anchor allows successful incorporation into liposomes, or into a cell membrane, its process of production is laborious, since it involves post reaction of the MAP core-peptide conjugate onto the lipid anchor by an esterification reaction, and furthermore the ester linking group is subject to hydrolysis in vivo and the entire molecule may therefore have a limited life span.

At the same symposium Huang et al describe another MAP with a built-in adjuvant. The dendritically linked poly(lysine) core was attached via a Ser-Ser spacer to three lysine residues and an alanine residue (from the peptide synthesis starting material). To the amine side chain functionalities of the lysine residues palmitoyl residues are joined in a subsequent amide-forming reaction. Huang et al describe an adaptation of the Tam homo poly(lysine) MAP core wherein the two amino ends of the lysine residues in the MAP have equal lengths by joining a β-alanine residue to the amino-acid amine group before subsequent reaction. The product molecule is said to allow free rotation of the peptides and to minimise surface interaction with a liposome into which the molecule is incorporated.

Although the product can be made by solid phase peptide synthesis alone, the reaction of the palmitoyl groups in a separate step increases the length of the overall process. In addition the difficulty in dissolving the starting material may cause problems.

It is known also that the delivery of drug molecules to the desired site of action in the body can be enhanced by increasing the size of the entity and/or by associating it with a drug delivery system (DDS). DDS can be particulate DDS, including liposomes, into which the drug is incorporated, for instance by dispersing it in the intra-vesicular space or by anchoring it to the liposome wall.

Liposomes as DDS may include on their surface components intended to affect the fate or destination of the liposome, for instance to prolong the circulation time in the blood, prevent or accelerate take up by certain tissues, or direct to particular receptors on a cell surface for instance by the use of hydrophilic coatings and/or attachment of antibodies.

It would be desirable to improve or facilitate the anchoring of these various active agents to liposome surfaces.

In WO-A-89/10348 (Gibbons), Tetrahedron (1992) 48, 923–930 (Toth et al) and Liebigs Ann. Chem. (1990) 1175–1183 (Gibbons et al), Gibbons et al describe the synthesis of lipidic amino acids and homo- and hetero-oligo peptides formed therefrom. The fatty amino acids have a side chain which is usually a $C_{6-24}$-alkyl or -alkenyl group, which may optionally be substituted. The peptides of the fatty amino acids are hydrophobic, water-insoluble but soluble in hydrophobic solvents and are said to be soluble in and compatible with natural membranes. Conjugation with pharmaceutical agents is suggested for increasing membrane solubility or translocation, enhancement of the activity of drugs that act at cell membranes or are absorbed through cell membranes and can be used as carriers for vaccines.

According to the present invention, there is provided a new peptide compound comprising at least 2 amino acid moieties joined together by peptide bonds, the compound comprising a lipophilic anchor which is connected to an amino acid moiety of the compound by a peptide bond and which comprises at least two amino acid moieties, each of the formula I

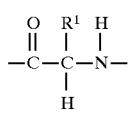

wherein each $R^1$ is independently a linear or branched chain alkyl or alkenyl group having 6 to 24 carbon atoms, the compound comprising also a matrix core section-comprising peptide bond linked amino acid moieties and having at least 2 terminal functionalities which are selected from —$NH_2$, —COOH, —OH, —SH and derivatives thereof.

The group $R^1$ may include substituents, provided these do not significantly adversely affect the lipophilic nature of the group. Suitable substituents include halogen, hydroxyl and thiol groups. It may be convenient to include substituents so as to confer upon the amino acid suitable solvent solubility properties to enable it to be used in peptide synthesis (for instance as described by Toth et al (op cit)).

The terminal functionalities which may be different, but are often the same, are generally selected from amine and carboxylic acid groups and derivatives thereof, usually derivatives which have removable protecting groups of the type commonly used in peptide synthesis. The protecting groups in a single molecule may be the same or different types. Most preferably, the terminal functionalities are each an amine group or a protected derivative thereof.

The lipophilic anchor section of the new compound may include two fatty amino acid moieties of the formula I or, preferably, may comprise 3 or even more such moieties, with $R^1$ groups which are the same or different, joined, preferably directly, to one another by peptide bonds. It may be optimal for the compound to comprise 3 such moieties, in order to mimic lipid compounds of biological membranes.

The matrix core section of the compound may comprise an unbranched chain of peptide-bond linked amino acids, each of which has a side group having a terminal functionality of the defined type. For instance the core may comprise an unbranched oligopeptide of an amino acid with a carboxylic acid-containing side chain or an amine group containing side chain, such as glutamic acid, aspartic acid or lysine. Each such unbranched chain must include at least two of the amino acid units, to provide at least two terminal functionalities.

Preferably the matrix core section comprises n levels of dendritically linked trifunctional amino acid moieties, in which n is an integer of 1 or more, preferably 2, 3 or 4, the trifunctional amino acid moieties comprising either two carboxylic acid groups or two amine groups. In this specification by "dendritically linked", we mean that the units are linked in a branched structure, at least one of the amino acid units at one level being linked by one of the two similar functionalities to two trifunctional amino acid units in the next level, optionally with spacer amino-acid residues in one or both of the branches between the two functionals of one level and the respect amino acid of the next level. For instance the single, central trifunctional amino acid of the first level is linked to one or two trifunctional amino acids in the second level. Where there are three or more levels, some or all of the maximum of four functionalities of the second level amino acids are joined to a further trifunctional amino acid moiety and so on. The core matrix thus has a maximum of $2^n$ terminal functionalities. n is preferably at least 2 and is usually 3 or 4, in which case the maximum number of terminal functionalities is 4, 8 or 16, respectively.

The amino acid unit on which a dendritic structure is based is preferably lysine. The branches may include spacer units, such as are described by Huang et al (op. cit.) so as to render the amino ends of a terminal residue or of an intermediate level of the dendritic structure, of substantially equal length. The spacer units suitably comprise β-alanine residues.

The dendritic structure need not be symmetrical, that is not every level of the structure need be complete.

In the invention, there must be at least two of the said terminal functionalities per molecule. The invention is of most benefit where there are at least 4 of the said terminal functionalities and it is often advantageous for there to be at least 8 or more.

The central trifunctional amino acid unit of a dendritic matrix core section may be joined via its third functionality (being the one different from the other two) to another amino acid unit, by a peptide bond.

Where the matrix core is a dendritic structure, the lipophilic anchor is preferably joined to the central amino acid, optionally via a linker group, although in some circumstances it may be preferable for the lipophilic anchor to be connected to the matrix core through one or more branches. Where the lipophilic anchor is joined through the central amino acid, a unit of the formula I may be joined directly to the central amino acid, through a peptide bond, or there may be an intermediate linker comprised of one or more amino acid units joined together by peptide bonds and joined to the fatty amino acid and to the matrix core by peptide bonds. For instance such linker amino acid moieties may give a desired spacing of the core matrix from the lipophilic anchor.

Where the matrix core section has a dendritic structure with the lipophilic anchor being joined directly or indirectly via one of its (C or N) terminals to the central amino acid, the opposite terminal of the lipophilic anchor may comprise one or several further amino acids joined together by peptide bonds. For instance such amino acids may be present as a result of the peptide synthesis procedure, where a particular amino acid was used as the first unit of a peptide chain in a solid state peptide synthesis using a commercially available loaded resin eg Boc-aminoacyl-pam-resin, or amino acyl BHA resin.

The terminal functionalities of the peptide compounds may be in the form of protected groups, such derivatives generally being temporarily protecting groups of the type used in peptide synthesis which can subsequently be removed. For instance amine groups as terminal functionalities may be protected by a carbobenzoxy group, or, preferably by t-butoxy carbonyl (Boc) or 9-fluorenylmethyloxy (Fmoc). Hydroxyl and thiol groups may be protected by benzyl groups. Carboxylic acid groups may be protected by different ester groups.

In a further aspect of the invention, there is provided a pharmaceutically active compound which is formed from a new peptide compound as defined above, having joined to each of the terminal functionalities a pharmaceutically active substituent.

In this aspect of the invention, although it may be convenient for each molecule to comprise two or more different pharmaceutically active substituents attached to terminal functionalities, the invention is of most benefit where each pharmaceutically active substituent in a single molecule is the same. The invention is of particular value where each of the pharmaceutically active substituents is a peptide antigen, that is where the pharmaceutically active compound is a multiple antigenic peptide. We have termed this new product a Lipid-Core Peptide (LCP). Preferably the pharmaceutically active substituent is bound to the peptide compound through peptide linkages with the terminal functionalities, which are accordingly carboxylic acid or amine groups or derivatives thereof. Alternatively, the pharmaceutically active substituent may be joined to the peptide compound via linker groups, such as an amino acid group or oligo peptide group, such as a triglycyl linker as described by Tam in PNAS (op. cit.).

The invention is of particular value when used as a synthetic peptide vaccine and in a further aspect of the invention a vaccine, for instance for immunoprophylaxis, comprises a pharmaceutically active compound according to the invention and a pharmaceutically acceptable carrier eg including an adjuvant, for instance CFA (complete Freund's adjuvant) or NAGO (neuraminidase and galactose oxidase).

The active ingredient may alternatively be a drug molecule which requires for optimal performance association with a drug delivery system.

In some circumstances, it may be desirable to include two different active substituents into a single molecule. For instance it may be advantageous to provide a molecule which has multiple valency antigenicity, where improved prophylaxis is achieved by raising antibodies to more than one epitope, as described by Di Marchi et al (op cit), for propylaxis or treatment of a single disease or for simultaneous prophylaxis or treatment of more than one disease.

It is believed that this is the first time it has been suggested to use the MAP system to produce a multivalent vaccine and according to a further aspect of the invention, there is provided a multivalent compound comprising a dendritically linked poly peptide core having at least two levels, and at least three terminal branches, an anchor comprising lipophilic components covalently linked to a backbone chain portion which is directly or indirectly covalently linked to the core, and two or more active substituents covalently linked to the terminal branches of the core. Preferably the multivalent compound is formed from a peptide compound of the first aspect of this invention.

Where two or more active substituents are included in the compound, this can be achieved by the use of a starting peptide compound wherein the terminal functionalities to which the different substituents are joined are different or are the same but which have different protective groups which can be removed under different conditions. For instance where the terminal functionalities are both amine groups, the protecting groups can include Boc and Fmoc.

The new peptide compound of the invention or the new pharmaceutically active compound may be presented in the form of a liposome composition, which comprises the new compound anchored in a lipid vesicle via the lipophilic anchor section. Any pharmaceutically active substituent may be on the surface of the lipid vesicles or may be in the intra-vesicular space.

In another aspect of the invention, there is provided a new process for producing the peptide compound according to the invention in which the lipophilic anchor and the matrix core section are linked by the reaction of the amine or carboxylic acid equivalent of the lipophilic anchor with the carboxylic acid or amine equivalent, respectively, of said amino acid moiety of the compound to form said peptide bond. Preferably the formation of said peptide bond is carried out as a solid phase peptide synthesis step in which the forming peptide compound is attached to a resin. Preferably the entire polypeptide is built up by a step wise peptide synthesis procedure from the respective amino acids, i.e. the process comprises the formation of peptide bonds between the moieties of formula I and of peptide bonds between the amino acid moieties of the matrix core section, sequentially and without cleavage of the forming peptide compound from the resin. Appropriate C and N-group protection and functional group protection of the terminal functionalities are used where necessary for forming the matrix core and anchor sections. Where the peptide compound is a pharmaceutically active compound wherein each terminal functionality is an amine or carboxylic acid group or derivative thereof, preferably each peptide bond which joins a pharmaceutically active substituent to a terminal functionality is formed by the reaction of amine or carboxylic acid moiety or derivative thereof of said pharmaceutically active substituent with said terminal functionality whilst the forming peptide compound is attached to the resin.

Although the process may be carried out in a liquid phase reaction, a solid phase reaction is far more convenient in general. A suitable process is a step wise solid phase reaction based on the procedure described by Merrifield in J. Am. Chem. Soc. (1963) 85, 2149–2154, or, preferably the development of that method as described by Mitchell et al in J. Org. Chem. (1978) 43, 2845–2852 using a resin with a phenylacetamidomethyl (Pam) bridge between the poly (styrene-divinyl-benzene) resin and the amino acid. It is preferred for the starting resin to have a relatively low amino acid content resin.

In the process, the or each fatty amino acid unit are preferably joined in steps prior to the reaction of the amino acids to form the matrix core section, although it may be joined in steps following the formation of the matrix core section. Linker amino acids may be incorporated in steps before and/or after the steps of adding the fatty amino acid units and/or the matrix core units.

The peptide-link forming steps may be any of those conventionally used in peptide synthesis. For instance the p-nitrophenyl ester method described initially by Bodansky in Nature (1955) 175, 685 may be used, or, more conveniently, the N, N'-dicyclohexylcarbodiimide method first described by Sheehan et al in J. Am. Chem. Soc. (1955) 77, 1067.

It is particularly convenient for the process to involve firstly the coupling of the N-protected one or more fatty amino acid units to the resin, with appropriate intermediate de-protecting procedures, followed by the formation of a matrix core unit, for instance which comprises a dendritic structure, by sequential formation of the levels of the core matrix using N-protected trifunctional amino acids again with suitable deprotecting steps in between the formation of the levels of the dendritic structure.

Where the dendritic structure includes spacer units in one but not the other branch of a unit at a particular level, for instance to introduce a β-alanine residue to equalise the branch lengths of a lysine residue, the two similar functional groups are provided with different protecting groups. For instance there is commercially available a lysine derivative which has one of its amine groups protected with a Boc group and the other protected by a Fmoc group. This allows the spacer residue to be added to one but not the other amine group. Where there is no spacer or a spacer for each branch the two similar functionalities should have the same protecting group. Where the pharmaceutically active compound is to include more than one type of active substituent the terminal functionalities of the peptide compound should be selected so as to be different or the same but with different protective groups, to allow sequential reaction of the different active substituents.

Subsequently the terminal functionalities may be reacted with a pharmaceutically active moiety after any necessary deprotection whilst the oligo peptide is still attached to the solid support, with an optional linker amino acid or several linker amino acids being incorporated in sequential steps if necessary. A pharmaceutically active moiety which is itself a peptide may be preformed and then added to the terminal functionalities, or may be synthesised in situ by stepwise formation using the same peptide synthesis steps. The oligo peptide can be removed from the solid support by known procedures and purified and recovered as necessary. For instance the procedures described by Merrifield (op. cit.) of saponification using ethanolic sodium hydroxide following deprotection in HBr/acetic acid or more usually, using the HF method described by, inter alia Tam et al in Tetrahedron Lett. (1982) 23, 2939–2942, or using the trifluoromethane-sulphonic acid-trifluoroacetic acid-dimethylsulphide technique described by Tam et al in J. Am. Chem. Soc. (1986) 108, 5242–5251.

The fatty amino acids from which the lipophilic anchor is derived may be any of those fatty amino acids described in WO-A-89/10348, Toth et al (op. cit.) and Gibbons et al (op. cit.). The fatty amino acids may be in the D- or L-form or may be a racemate. It may be advantageous to use alternating D- and L-fatty amino acids in a peptide compound including two or more adjacent residues as explained by Huang et al.

It has been found that, despite the lipophilic nature of the fatty amino acid compounds, solid phase peptide synthetic procedures can be used to form the compounds of the invention as the monomeric fatty amino acids are soluble in the liquid vehicles conventionally used.

Although solid-phase peptide synthesis is preferred for the process of the invention, it is alternatively possible to use liquid-phase procedures for some or all of the steps for forming the peptide compounds of the invention.

The peptide compound of the present invention may be attached to a solid support as an article of commerce. For instance it may be convenient to supply the compound in the form of a resin support, of the type generally used for solid-phase peptide synthesis, to which is attached the peptide compound, which is the direct result of a solid-phase reaction process. In the most preferred form of the invention, the compound will comprise the resin support linked directly or via a linker peptide moiety to the lipophilic anchor, which is in turn either directly or via a peptide linker joined to the core matrix, which generally comprises a dendritic structure, the central amino acid of which is directly or indirectly attached to the lipophilic anchor. In this form of the compound, the terminal functionalities are generally amine groups, or carboxylic acid groups, in protected form, the protecting groups being those normally used in peptide synthesis for temporary protection, and which are generally the direct products of the peptide synthesis steps. The compound in this form is relatively stable and can be sold as an article of commerce, for subsequent reaction with pharmaceutically active substituents, especially antigenic peptides or for synthesis in situ of antigenic peptides, followed if desired by cleavage of the product compound from the solid support.

A particularly preferred embodiment of the invention is represented by the formula

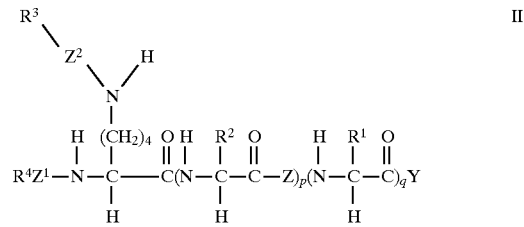

II wherein Z, $Z^1$ and $Z^2$ are independently selected from a bond, an amino-acid residue and an oligopeptide residue, $R^3$ and $R^4$ are independently selected from H, an amine protecting group, a pharmaceutically active moiety, and a group III

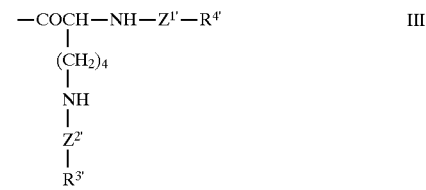

III wherein $R^{3'}$, $R^{4'}$, $Z^{1'}$ and $Z^{2'}$ are selected from the same groups represented by $R^3$, $R^4$, $Z^1$ and $Z^2$, respectively, p is 0 or an integer, the or each $R^2$ is independently selected from linear and branched chain alkyl and alkenyl groups having 6 to 24 carbon atoms and naturally-occurring amino acid side chains, q is an integer of at least 1 the or each $R^1$ is independently selected from linear and branched chain alkyl and alkenyl groups having 6 to 24 carbon atoms, Y is OH, $NH_2$, a carboxylic acid protecting group or comprises an amino acid or oligopeptide moiety and/or a resin on which the peptide has been synthesised.

Preferably p is 0 or 1. Where p is 1, —NHCHR$^2$COZ— is preferably an oligopeptide moiety of 2 or 3 amino acid units.

Preferably q is 2 or 3.

Preferably $R^3$ and $R^4$ are each a group of the formula III.

In one preferred embodiment in which $R^3$ and $R^4$ are each a group of the formula III in which $R^{3'}$ and $R^{4'}$ are also groups of the formula III, in the latter groups it is preferred that $R^{3'}$ and $R^{4'}$ are independently selected from H, amine protecting groups and a pharmaceutically active moiety, preferably each $R^{3'}$ being the same group and each $R^{4'}$ being the same group, which is the same or different from the $R^{3'}$ group.

In the compound, any amine protecting groups are preferably selected from Boc and Fmoc.

$Z^2$ and $Z^{2'}$ are preferably bonds.

$Z^1$ and any $Z^{1'}$ groups are each preferably selected from a bond and a β-alanyl residue.

In one preferred embodiment, Y includes a resin moiety, $R^3$ and/or $R^4$ represent a group of the formula III and any $R^{3'}$ and/or $R^{4'}$ groups represent an amine protecting group or a group of the formula III in which any $R^{3'}$ and $R^{4'}$ groups represent an amine protecting group.

In another preferred embodiment, Y is OH, $NH_2$, a carboxylic acid protecting group or an amino acid or oligo peptide moiety, which may have a carboxylic acid protecting group, $R^3$ and/or $R^4$ represent a group of the formula III in which any $R^{3'}$ and $R^{4'}$ groups represent a pharmaceutically active moiety or a group of the formula III in which any $R^{3'}$ and $R^{4'}$ groups represent a pharmaceutically active moiety.

The pharmaceutically active moiety is generally joined to the nitrogen atom of the amine group by a peptidyl bond. The pharmaceutically active moiety is generally a peptide group, preferably an antigenic peptide moiety. It may alternatively be a drug molecule.

EXAMPLE 1

Figure 1:
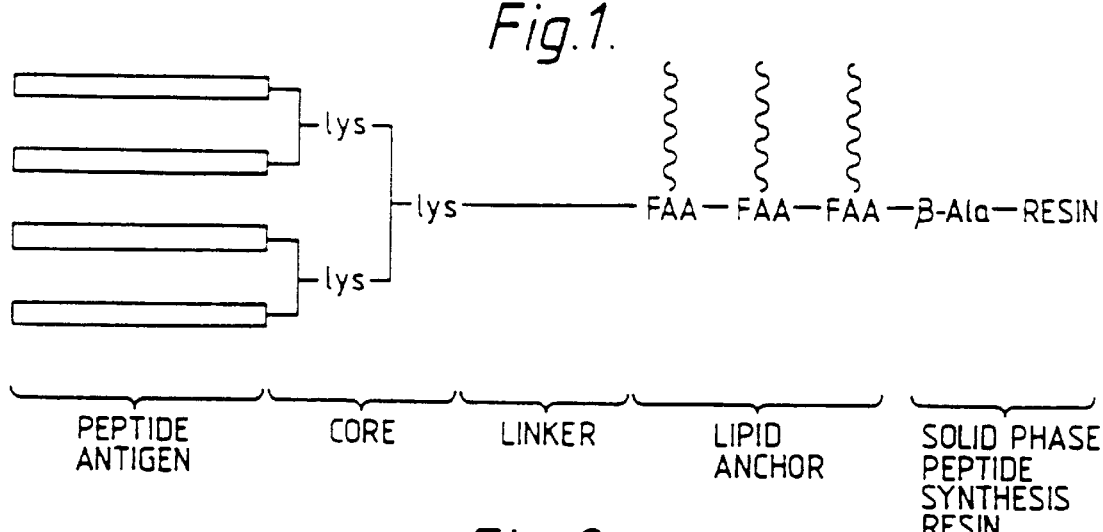
FIG. 1 illustrates one embodiment of the invention, having a core comprising dendritically linked lysine residues, of two levels and this having four branches, to each of which branches is attached a peptide antigen, and the core being attached via a linker region to three linked fatty amino acid (FAA) residues which in turn are linked via a β-Alanyl residue to the resin being the resin used in the solid phase synthesis of the peptide. The peptide antigen moieties may be the same or different. The β-ala residue can be omitted.
Figure 2:
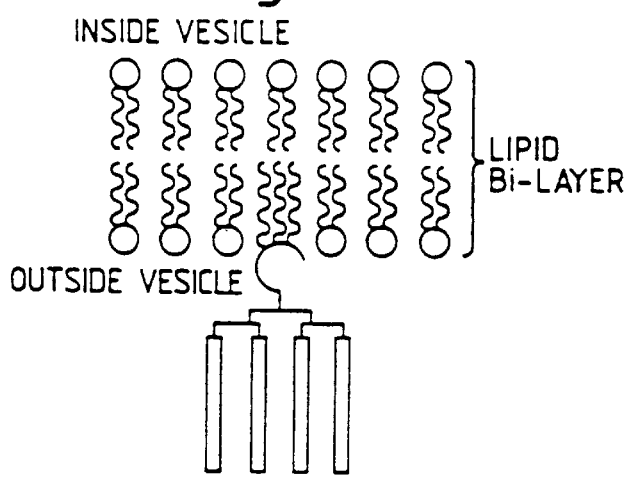
FIG. 2 shows the compound of FIG. 1 incorporated into a lipid vesicle (a liposome), the lipid anchor of the lipophilic side chains of the fatty amino acids being incorporated into the lipid bi-layer wall of the liposome. In both FIGS. 1 and 2 the peptide moieties may alternatively be drug moieties.
Figure 3:
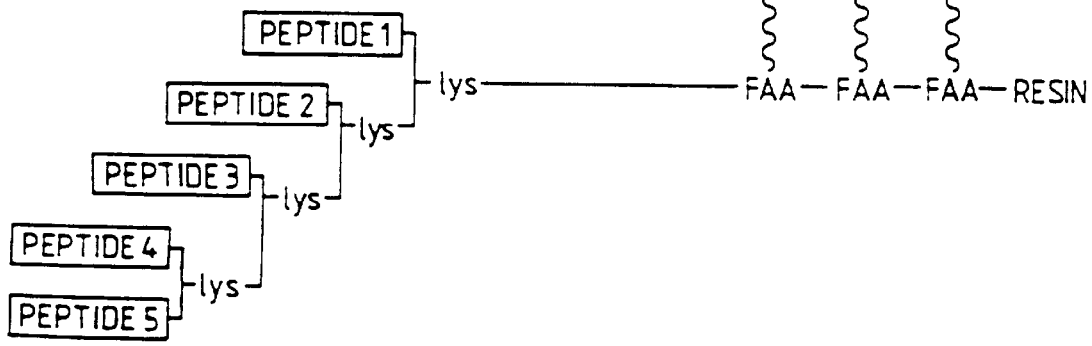
FIG. 3 shows a multivalent vaccine comprising a core of dendritically linked lysine residues, with at each level one branch attached via the terminal —$NH_2$ group to a peptide and one branch attached to another lysine. Thus each level of the core comprises a single residue of lysine and there are one more different peptides as there are levels.

Synthesis of (Peptide)$_8$Lys$_4$Lys$_2$Lys{HNCH[$(CH_2)_{13}CO$]$_3$NH$_2$ [LCP]

Techniques

The Boc-NH-CH[$(CH_2)_{13}CH_3$]COOH was synthesised from 1-bromododecane (Gibbons et al. Liebigs Ann. Chem. 1990 1175–1183).

Peptide Synthesis

The peptides P1 to P5 (see below) and LCP's were synthesised stepwise on solid phase using Novabiochem MBHA resin.

An Applied Biosystems 430A Automated Synthesizer involving the SPPS techniques of Merrifield or modification thereof, was used. Basically, the growing peptide chain is bound covalently through its C-terminus to the insoluble solid support, namely the 4-methylbenzhydrylamine (MBHA) resin. Synthesis was carried out by the successive addition of blocked amino acids in the desired sequence. Standard HF cleavage was carried out to release peptides from resin. Coupling efficiency of synthesis was monitored by quantitative ninhydrin assay.

The peptide H1 (see below) was synthesised using a Fast MOC HBTU/NMP chemistry.

Purification and characterisation of the peptides

All of the peptides cleaved from resin were purified by standard FPLC/HPLC techniques involving ion-exchange (e.g. DEAE) and gel filtration (Sephadex G-25 or G-50) chromatography. C4 or C18 reverse phase HPLC was used for large scale purification. Quality control for purity and correct sequencing of the peptides was carried out by HPLC analysis and Fast gel electrophoresis. Additional criteria were FAB MS, NMR, IEF. For 'large' proteins gas phase microsequencing was used to confirm the correct sequence.

Infra-red spectra were recorded with a Perkin Elmer 841 spectrophotometer. $^1$H-NMR spectra were obtained on Varian ZL-300 and Bruker AM500 instruments operating at fields of 300 and 500 MHz respectively; Mass spectra were run on a VG Analytical ZAB-SE instrument, using fast atom bombardment (FAB) ionisation. Reaction progress was monitored by ninhydrin test.

Peptide purification: Analytical HPLC separation was carried out on a Vydac $C_{18}$ 5 RAC column. HPLC grade acetonitrile (Aldrich) and water were filtered through a 25 μm membrane filter and degassed with helium flow prior to use. Analytical separation was achieved with a solvent gradient beginning with 0% acetonitrile, increasing constantly to 60% acetonitrile at 30 minutes, staying at this concentration for 20 minutes and decreasing steadily to 0% acetonitrile for 10 minutes at a constant flow of 0.7 ml min$^{-1}$. For preparative separation TSK-GEL semipreparative $C_{18}$ column was used, separation was achieved with a solvent gradient beginning with 0% acetonitrile, increasing constantly to 60% acetonitrile at 180 minutes, staying at this concentration for 60 minutes and decreasing steadily to 0% acetonitrile for 30 minutes at a constant flow of 7 ml min$^{-1}$. The gradient was effected by two microprocessor-controlled Gilson 302 single piston pumps. Compounds were detected with a Holochrome UV-VIS detector at 218 nm (analytical) and 230 nm (preparative). Cromatographs were recorded with an LKB 2210 single channel chart recorder.

Synthesis Method

The synthesis of (Peptide)$_8$Lys$_4$Lys$_2$Lys{HNCH[$(CH_2)_{13}CH_3$]CO}$_3$NH$_2$, was accomplished automatically by a stepwise solid phase procedure on MBHA Novabiochem resin (substitution 0.48 mmol/1 g resin). The synthesis of the first and every subsequent level (i.e. of the fatty amino acids, the poly(lysine) dendritic core and the antigenic peptide) of the peptide construction was achieved using 4M excess of preformed symmetrical anhydride of N-Boc amino acids in dichloromethane (15 ml) followed by a second coupling in dichloromethane (20 ml)/N-methylpyrrolidone (5 ml). The protecting groups for the synthesis of the peptide construction were Boc groups for the α-amino-termini, Bzl(benzyl), Tos(tosyl), Br-Z, (2-bromobenzyl-p-nitrophenylcarbonate), OBzl, CHO, Cl-Z (2-chlorobenzylocycarbonyl), DNP, (2,4-dinitrophenyl), 4MeBzl, (4-methylbenzyl), Acm (acetamidomethl) and Bom (benzyloxymethyl) for the amino acids. For all residues the coupling, monitored by quantitative ninhydrin test was done with the preformed (DCC) symmetrical anhydride or with the assistance of hydroxybenzotriazole in $CH_2Cl_2$, a second coupling in dichloromethane, DMF or dichloromethane/N-methylpyrrolidone. After the second coupling deprotection of the N-termini was performed in 65% TFA in dichloromethane. The deprotected resin peptide was neutralized with 10% diisopropylethylamine in dichloromethane. The peptide construction was removed from the resin support with high (1.5 ml cresol, 1.5 ml thiocresol, 20 ml HF) or low-high HF method (1.5 ml cresol, 1.5 ml thiocresol, 20 ml methylsulphide, 10 ml HF-1.5 ml cresol, 1.5 ml thiocresol, 20 ml HF) to yield the crude peptide construction, which was precipitated with ether or ethylacetate and redissolved in 90% acetic acid (20 ml). The crude peptide construction was purified by semipreparative HPLC method.

Figure 4:
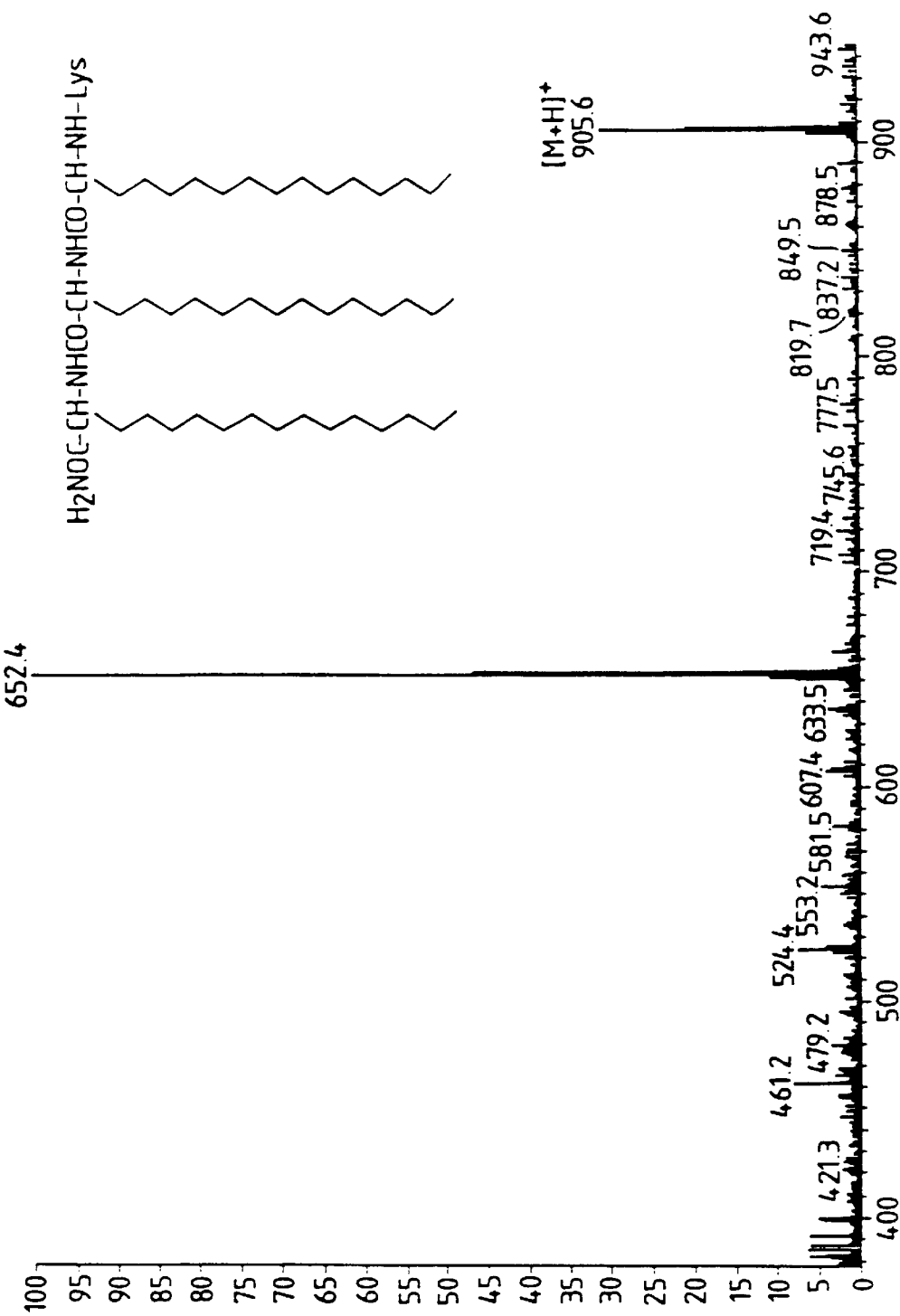
FIG. 4 illustrates the mass spectra of the lipid core intermediate Lys-{HNCH[$(CH_2)_{13}CH_3$]CO}$_3$NH$_2$.
Figure 5:
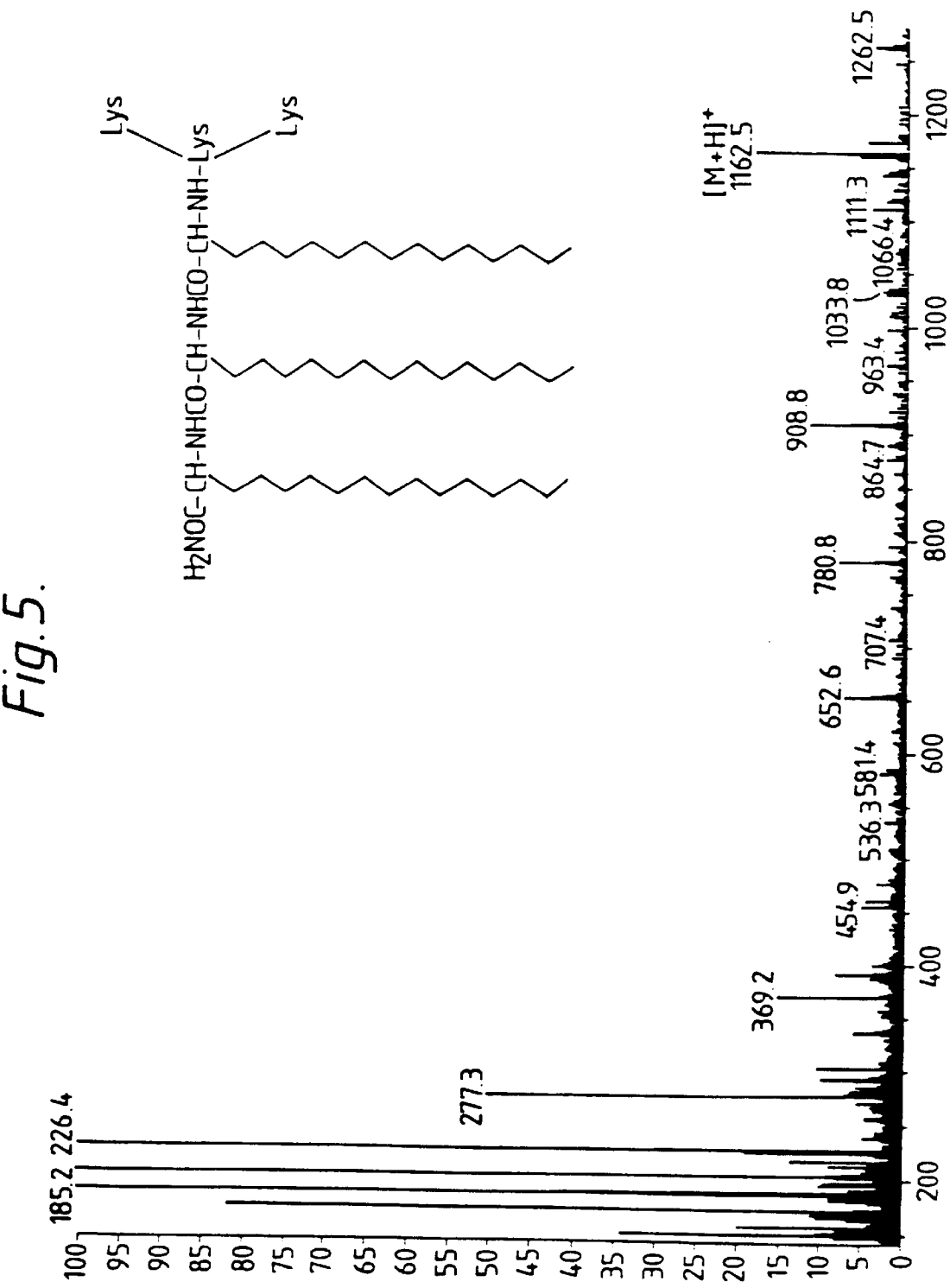
FIG. 5 illustrates the mass spectra of the lipid core intermediate Lys$_3$-{HNCH[$(CH_2)_{13}CH_3$]CO}$_3$NH$_2$.
Figure 6:
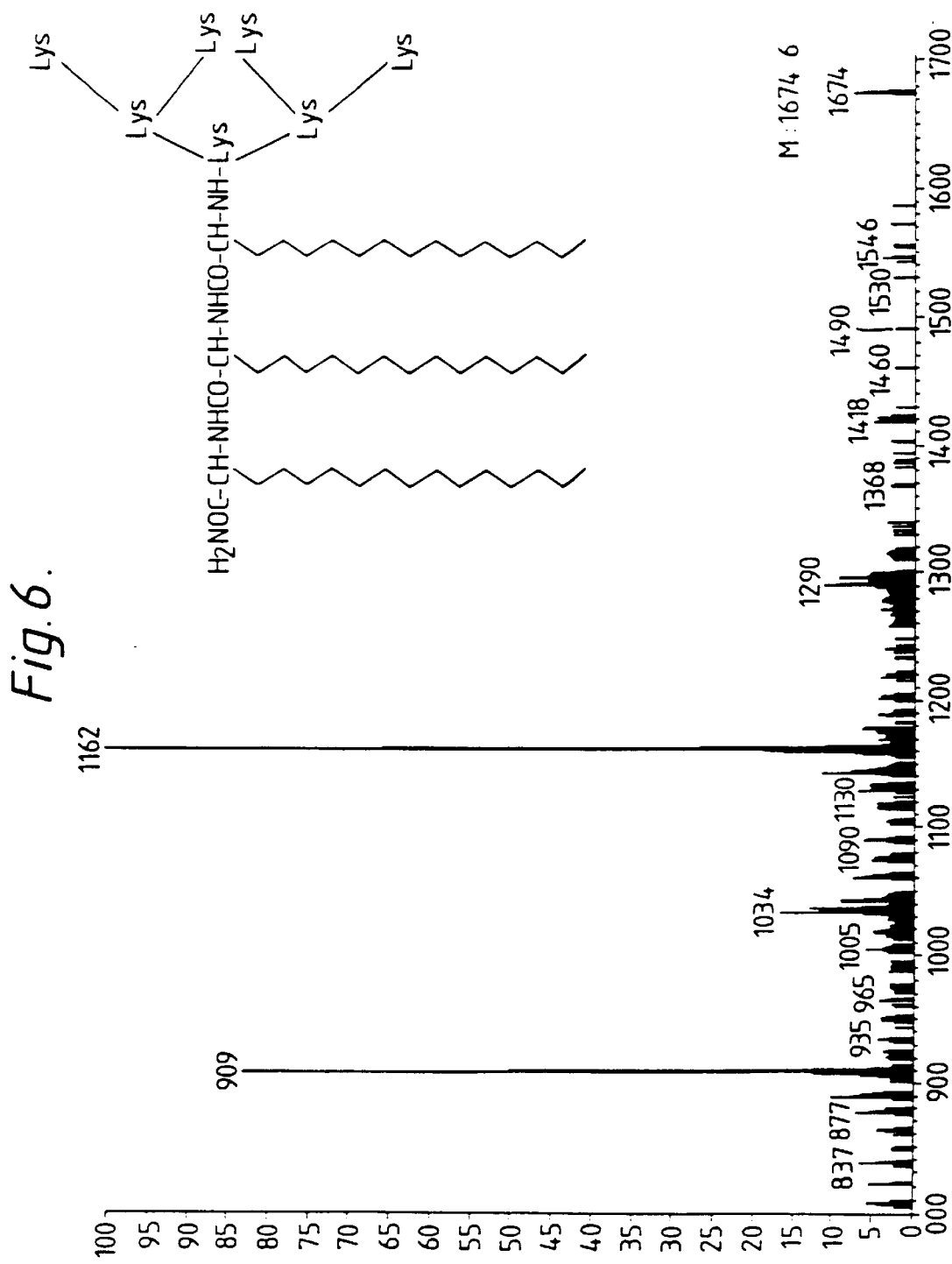
FIG. 6 illustrates the mass spectra of the lipid core intermediate Lys$_7$-{HNCH[$(CH_2)_{13}CH_3$]CO}$_3$NH$_2$.

Analysis of Lipid-Core (MS):

FIGS. 4 to 6 illustrate mass spectra of the three lipid-core intermediates.

Lys-{HNCH[(CH$_2$)$_{13}$CH$_3$]CO}$_3$NH$_2$ FIG. 4
Lys$_3$-{HNCH[(CH$_2$)$_{13}$CH$_3$]CO}$_3$NH$_2$ FIG. 5
Lys$_7$-{HNCH[(CH$_2$)$_{13}$CH$_3$]CO}$_3$NH$_2$ FIG. 6

Production of antibodies against the peptides.

Conjugation of carrier protein with peptides for comparison with the LCP system:

To increase the immunogenicity of the peptides and meet the requirement of ELISA for antibody assay, the carrier proteins were conjugated to the peptides. KLH was chosen as the immunogen carrier and BSA in the ELISA experiments. The glutaraldehyde method was adopted, but other conjugating agents such as SPDP, water soluble carbodiimide etc. may be used if necessary. The unused coupling agent was removed by passing through Sephadex G-25 column. Conjugated samples were lyophilized and kept at −18° C.

Production of antibodies

The LCP system was injected directly. Rabbits were used to produce polyclonal antibodies using the immunization protocol 1-21-35-60.

Antiserum test

Indirect ELISA tests for site-specific antibodies used ELISA plates coated with the peptide. Analogous experiments were carried out using ELISA plates coated with RBL-2H3 cells obtained in culture.

Isolation of Antibodies by ion-exchange and affinity chromatography

Where necessary affinity chromatography with protein A columns or peptide coupled Sepharose CL-4B columns were used to isolate antibody to each peptide. The purity of the antibodies was analysed by SDS-PAGE.

Immunogenicity of Chlamydia trachomatis major outer membrane Protein (MOMP) Peptides The B cell antigenicity of 7 MOMP sequences was evaluated using synthetic peptides (Pepscan) and polyclonal antisera from rabbits and mice and monoclonal antibodies from mice. The VDIV of all MOMPS contained multiple cross-reactive, immunodominant, surface exposed epitopes. VDI among C serogroup MOMPs was also immunodominant. T cell antigenicity was evaluated for serovar B MOMP in a lymphocyte proliferation assay using a cloned fragment containing 61 amino acids from B MOMP VDIV (RASFDADTIRIAQPKSAETIFDVTTLNPTIAGAGDV KTSAEGQLGDTMQIVSLQLN KMKSR$^{333}$). This cloned polypeptide fused with flutathione-S-transferase was able to stimulate an antigen specific T cell proliferation response. Five partially overlapping peptides (designated as P1 to P5) were synthesized with a length of 16 to 22 residues to cover this fragment. Three inbred strains of mice with different H2 haplotypes were used in an in vitro T cell proliferation assay. P1 (with sequence of $^{273}$RASFDADTIRIAQP KSAETIFDG) and P5($^{319}$TMQIVSLQLNKMKSRG) were recognised by H-$2^d$ strain BALB/c and P2 ($^{289}$AETIFDVT TLNPTIAG) by both H-$2^k$ strain CBA and by H-$2^b$ strain C575BL/10. In an in vivo antibody promotion assay, P5 elicited high titer IgG antibody production only in BALB/c, P2 in both CBA and C57BL/10 while P1, P3 and P4 failed to stimulate antibody production in any of the strains. Thus P2 is a potential peptide for incorporation into a candidate chlamydia vaccine since its T cell site has the least host genetic restriction and it can promote antibody production to surface exposed B cell. epitopes within the peptide.

The immunogenicity of P2 sequence was further studied using the eightfold branched lysine core and attached to eight P2 peptide residues (designated as LCP-1). LCP-1 was used to immunize five congenic mouse strains. It elicited high titered antibodies in B10.A(H-$2^d$) and B10.BR(H-$2^k$) strains and low titered antibodies in B10(H-$2^b$) strain. Strains B10.D2(H.$2^d$) and B10.A(3R) (H.$2^{13}$) failed to produce antibodies to LCP-1. The LCP-1 raised antibodies from the strains H-$2^k$ and H-$2^d$ were able to recognise native epitopes on chlamydial EBs and displayed similar epitope specificities in Pepscan as antisera raised with whole EBs. These observations suggest that the LCP-1 preparation maximally enhanced immunogenicity of the P2-peptide; however LCP-1 peptide antibody responses were H-2 restricted.

Comparison

In order to incorporate surface-exposed epitopes from C sero-group serovars and to alter the H-2 restriction patterns a 30 mer co-linear peptide (designated as H1) was constructed, which incorporated C sero-group MOMP VDI epitope as a B cell epitope (for C-serogroup) and the P2 sequence as both B cell epitope (for B-serogroup) and T cell epitope. The sequence of H1 is SAETIFDVTTLNPTIAGS-DVAGLQNDPTTN. H1 peptide was able to engender chlamydia serovar A, B and C whole EB reactive antibodies in all tested five strains of mice with the highest antibody titer in B10.A H-$2^d$) and B10.BR(H-$2^k$). However H1 co-linear peptide is less immunogenic than LCP-1 as determined by antibody titer.

EXAMPLE 2

Further experiments were carried out using peptides P1 to P5 and H1 to confirm the results of example 1.

Organisms and Animals: C.trachomatis serovar A(G17//OT), B(TW5/OT), and C(TW3/OT) were grown in Hela 229 cells and EBs were purified from infected cells by density gradient centrifugation. The following strains of female mice were purchased from Jackson Laboratories (Bar Harbor, Me.) and used at 7–9 weeks of age: C57BL/10snj (H-$_2{}^b$); B10.A/sgsnj (H-$2^a$); B10.D2/j (H-$2^d$); B10.BR/sgsnj (H-$2^k$); SJL/j (H-$2^s$); Balb/cj (H-$2^d$); and CBA/j (H-$2^k$).

Solid Phase Peptide Synthesis: A set of five partially overlapping peptides with a length of between 15 and 20 residues covering a 61 residue sequence from B omp1 VD IV region was synthesised using t-Boc chemistry (as described in "Solid Phase Peptide Synthesis, 2nd Edn., Stewart and Young, eds.) and designated as P1 to P5. The sequences of the five peptides are as follows:

| VDIV of B $omp_1$ | |
|---|---|
| 273 333<br>RASFDADTIRIAQPKSAETIFDVTTLNPTIAGAGDVKTSAEGQLGDTMQIVSLQLNKMKR | |
| 273 294<br>RASFDADTIRIAQPKSAETIFDG | $P_1$ |
| 297 303<br>AETIFDVTTLNPTIAG | $P_2$ |

-continued

| VDIV of B $omp_1$ | |
|---|---|
| 297 313<br>TTLNPTIAGAGDVKTSAEG | $P_3$ |
| 304 324<br>KTSAEGQLGDTMQIVG | $P_4$ |
| 334 334<br>TMQIVSLQLNKMKSRG | $P_5$ |

P2 peptide was subsequently synthesised as a peptide chain extended with two lipidic amino acids, the P2 lipidic amino acid monomer ("P2 dimer") having the formula $H[NHCH\{(CH_2)_{13}CH_3\}CO]_2$-P2, and as a lipidic poly L-lysine LCP of the same formula as LCP-1 described in example 1. A 30-mer chimeric peptide containing a 13-mer sequence from C omp1 VD I in addition to P2 was synthesised using a Fast Moc HBTU/NMP chemistry ("Solid Phase Peptide Synthesis" mentioned above). The chimeric peptide was designated H1 and was synthesised as a dimeric lipidic amino acid H1 and as a lipidic poly L-lysine LCP-H1, these having corresponding formulae with the P2 dimer and LCP respectively.

Immunisation of Mice: Antisera were raised to serovar B or C EBs in mice as described by Zhong and Brunham, Infect. Immun. 60:3143, 1992 (Publication A). Anti-peptide antisera were raised in groups of 4–6 mice from each strain injected with 50 μg of each peptide preparation i.p. (P1 to P5, 25x LCP-P2, H1 and LCP-H1) emulsified in CFA (complete Freund's adjuvant) on day 0, and boosted with 50 μg of the same antigen in IFA (incomplete Freund's adjuvant) on days 14 and 28. Sera were collected 14 days after final injection. Sera from each group were pooled, aliquoted and stored at −20° C. until use. The potency was tested of adjuvant NAGO (neuraminidase and galactose oxidase) in B10 mice. NAGO adjuvant was prepared as follows: 1 unit of NA (cat# N-2133, Sigma Chemical) and 5 units of GO (cat# G3385, Sigma Chemical) in 100 μl of PBS containing 50 μg MAP-H1 peptide were mixed immediately before injection. The mixture was administered s.c. (tail base) with 50 μg peptide per injection per mouse. The injection was repeated twice at 14 day intervals. Sera were collected on the 14th day after each injection. Normal mouse sera were collected from each strain and used for control.

Lymphocyte Proliferation Assay: Lymphocyte proliferation assay was carried out as described by Zhong and Brunham in Infect. Immun. 60:1221, 1992 (Publication B). Each mouse was immunised with $5\times10^5$ inclusion forming unit (IFU) of serovar B EBs emulsified with an equal volume of CFA by foot pad injection. Two weeks following the injection, popliteal lymph nodes from both specific antigen immunised and PBS (pH 7.4)-CFA emulsion injected control mice were harvested and cellular suspensions were prepared. T cells were enriched by passing the cell suspensions through a nylon wool column. Four$\times10^5$ T cells and $10^5$ syngeneic irradiated ($Cobalt^{80}$, 2000 rad) peritoneal macrophages were cultured with serial dilution of peptide antigens in a total volume of 0.2 ml medium in microtiter plates at 37° C. in 5% $CO_2$ for five days. The cultures were pulsed by adding 1 μCi per well [$^3$H]-thymidine (6.7 Ci/mmol; New England Nuclear) for the final 16 hours. The cells were harvested onto glass fibre filters and the incorporation of [$^3$H]-thymidine into DNA was counted. The results were expressed as SI (stimulation index, dpm of experimental cultures divided by dpm of control cultures).

Immunoblot and Immunodot blot: The immunoblot assay for detecting antibody binding to membrane-immobilised protein from clamydial organisms was carried out as described in Publication A. The dot blot assay was done as described by Zhang et al (J. Immunol. 138: 575, 1987) except for the following modifications: $2\times10^5$ IFU serovar A, B or C EBs were dotted onto the nitrocellulose membrane in 50 μl sucrose-phosphate-glutamate (SPG). The membrane was blocked with 4% bovine serum albumin and 0.05% Tween-20 in PBS (pH 7.4) (blocking solution). Both antisera and iodinated conjugates were diluted with 2% bovine serum albumin and 0.05% Tween-20 in PBS (incubation solution) A mixture of goat antimouse IgG conjugated with $^{125}$I (cat.#168075, ICN Biochemicals, CA) and $^{125}$I-protein G (cat.#168089, ICN biochemicals, CA) was used to visualise the antibody binding.

ELISA: Microtiter plates (Immulon 2, 96-round-U-well, Dynatech Laboratories, Alexandria, Va.) were coated overnight at 4° C. with $10^6$ IFU/well of native EBs in 100 μl of SPG or 1 μg/well of peptides of 100 μl of PBS. The plates were washed with 200 μl of SPG or PBS once and blocked with 200 μl/well of blocking solution at 37° C. for 90 minutes. Serial dilutions of antisera were made in incubation solution and added to the plates at 100 μl/well. The plates were incubated at 37° C. for 60 minutes. After washing four times with 200 μl/well of wash solution (0.05% Tween-20 in PBS, pH 7.4), goat anti-mouse IgG-peroxidase conjugate (Pierce, Ill.) at 1:4000 dilution in incubation solution was added at 100 μl/well and the plates incubated as before. After washing as before, 100 μl of substrate [2.2-azino-bis-(3-ethyl-benzthiazoline-6 sulphonate) in citrate buffer (pH 4.5) in the presence of $H_2O_2$] was added to each well. The enzymatic reaction was developed for 15 minutes at room temperature and absorbance was measured at 405 nm on a Titertek Multiskan plus version 1.43 automatic ELISA reader (EFLAB, Finland).

In vitro Neutralisation Assay: Neutralisation was assessed in a HAK cell (Hamster kidney cell line from NIH)-in vitro neutralisation assay as described by Su et al (Infect. Immun. 59:2843 and 59:3811, 1991). Briefly neutralisation assays were done by preparing serial 2-fold dilutions of antisera in SPG. A pooled normal mouse serum was similarly diluted and used as control. An equal volume of EBs (EBs were titrated and adjusted to $2\times10^4$ IFU/ml in SPG) was mixed with an equal volume of antisera dilutions and incubated at 37° C. for 30 minutes. A 50 μl volume of the mixtures was inoculated in triplicate onto monolayers of HAK cells grown for 24 hours in 96-well plates with flat bottoms (Nunclon, Denmark) and incubated at 37° C. for 2 hours. The inoculum was removed and the monolayers were washed with prewarmed HBSS. The cells were fed with 200 μl of MEM containing 10% fetal calf serum and 1 μg of cyclohexamide per ml and incubated for 48 hours at 37° C. After fixation of the monolayers with methanol, chlamydial inclusions were detected by staining with a rabbit anti-chlamydial serovar A, B, and C polyclonal antisera (1:1000) as the first antibody, horseradish peroxides conjugated goat anti-rabbit antibodies as the secondary antibody and 1-chloronaphthanol (Sigma Chemicals) as the substrate. IFUs were quantitated by counting 5 fields at a magnification of 200× using an inverted microscope. An average of IFU number per field was calculated from three plates and the results were expressed as percentage of reduction of IFU numbers compared to control wells.

Identification of T Helper Sites in omp1 Peptides: In a preliminary experiment, a cloned fusion fragment containing a 61 amino acid sequence from position 273 to 333 of serovar B omp 1 was found to recall an antigen-specific proliferation response of T cells primed in vivo with chlamydial EBs in Balb/cj (H2 $^d$) mice. The 61 amino acid sequence covers the entire VD IV region of serovar b omp 1. Five partially overlapping peptides (labelled $P_1$ to $P_5$) covering the entire 61 amino acid sequence were synthesised and used to localise potential T cell sites. Three inbred strains of mice, each representing a different H-2 haplotype were used in the study. As shown in Table 1 below, $P_1$ and $P_5$ stimulated significant proliferation responses in Balb/c (H-$2^d$) but not in C57BL/10 (H-$2^b$) or CBA (H-$2^k$) mice; $P_2$ stimulated significant proliferation responses in both CBA (H-$2^k$) and C57BL/10 (H-$2^b$) but not Balb/C (H-$2^d$) mice; $P_3$ and $P_4$ failed to stimulate proliferation in any of the three strains of mice. Thus the T cell site in $P_2$ can be presented by H-$2^b$ and H-$2^k$ but not by H-$2^d$.

Effects of Incorporation into LCP on Immunogenicity of P2 peptide: Since P2 contains both B cell epitopes and T helper sites, the effects of polymer construction on immunogenicty of the synthetic peptides was evaluated. LCP-P2 was constructed with a three fatty amino acid chain attached to the C-terminus of the initial lysine. The immunogenicity of LCP-P2 was compared with the P2 peptide synthesised to two fatty amino acids (P2 dimer).

P2 dimer and LCP-P2 were used to immunise four congenic strains of mice. The antisera were assayed against serovar B EB whole organisms in ELISA, results in Table 2 below.

TBLE 2

| Mouse Antisera | B10 | | B10.A | | B10.BR | | B10.D2 | |
|---|---|---|---|---|---|---|---|---|
| Peptide Construct | P2-Dimer | LCP-P2 | P2-Dimer | LCP-P2 | P2-Dimer | LCP-P2 | P2-Dimer | LCP-P2 |
| Antibody Titer (−Log concentration) | 1.60 | 2.50 | 1.60 | 3.70 | 1.90 | 3.40 | — | — |

Figure 7A:
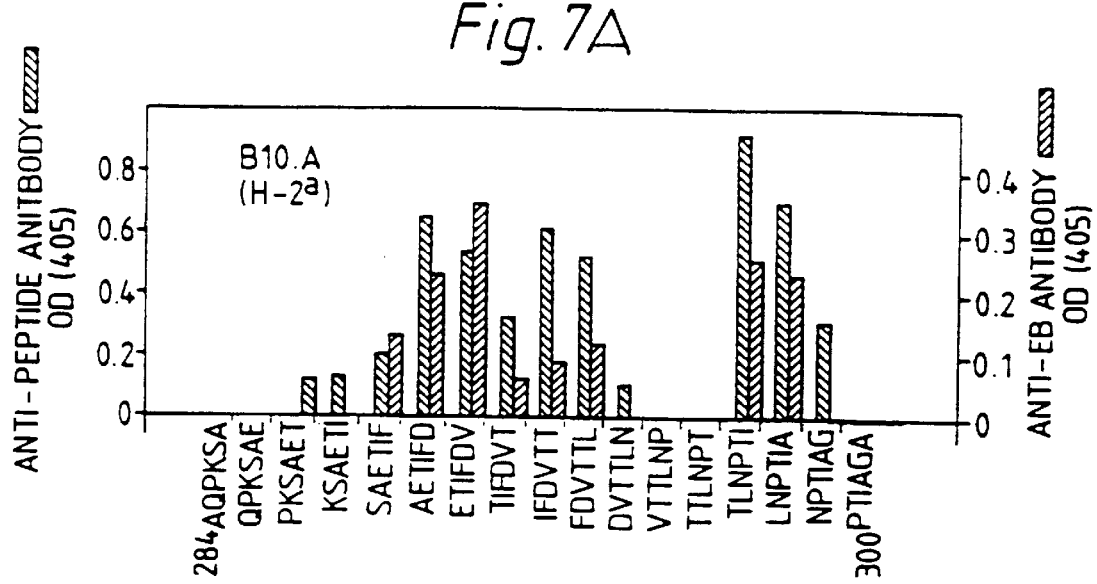
FIGS. 7A and 7B each is a mapping described below with respect to the effects of incorporation into LCP on immunogenicity of $P_2$ peptide.
Figure 7B:
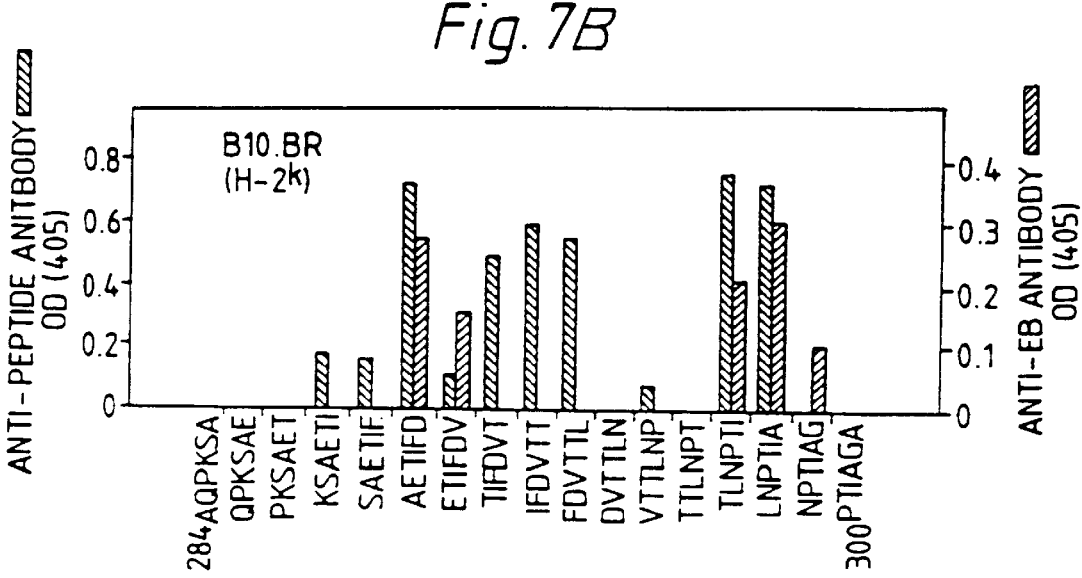

P2 elicited anti-EB antibodies with relatively low titers while LCP-P2 was able to raise antibodies with high titers in B10.A and B10.BR and intermediate titers in B10. B10.D2 (H-$2^d$) restriction of immune response observed with the P2 peptide (Table 1). In a pepscan assay, antisera raised with LCP-P2 in two high responder strains displayed similar epitope specificities as antisera raised with whole serovar B EBs except that more epitopes were mapped with LCP-P2 antisera (FIGS. 7A and 7B). LCP-P2 antisera were tested at 1:500 dilution and the anti-EB antisera at 1:200.

The two major epitopes recognised by both serovar B EB and LCP-P2 antisera were the B serogroup and species

TABLE 1

| Mouse Strain | Balb/C (H-$2^d$) | | | | | C57/BL.10 (H-$2^b$) | | | | | CBA (H-$2^k$) | | | | |
|---|---|---|---|---|---|---|---|---|---|---|---|---|---|---|---|
| Peptide | P1 | P2 | P3 | P4 | P5 | P1 | P2 | P3 | P4 | P5 | P1 | P2 | P3 | P4 | P5 |
| Stimulation Index | 3.2 | 1.2 | <1 | 1.6 | 4.10 | <1 | 2.95 | <1 | 1.05 | 1.50 | 1.45 | 3.05 | 1.65 | 1.05 | 1.35 |
| Antibody Titer (−Log concentration) | — | — | — | — | 3.15 | — | 2.75 | — | — | — | — | 1.95 | — | — | — |

It has been suggested that the induction of IgG responses to a small peptide antigen is an in vivo assay of the activity of Th2 cell subpopulations since only a peptide containing both T helper and B cell sites is able to induce IgG response. As shown in Table 1, $P_5$ was able to elicit serovar B specific antibody in Balb/C (H-$2^d$) mice; $P_2$ elicited serovar B specific antibody in both C57/BL.1.0 (H-$2^b$) and CBA (H-$2^k$) strains confirming its T cell site activities in these two strains; $P_1$ failed to evoke serovar B antibody in any strain although it exhibited a T cell site activity in Balb/c (H-$2^d$) mice.

In aggregate, the observations show that T cell sites exhibit variable H-2 restriction patterns. H-2 restriction on T cell sites may contribute to H-2 dependent antibody responses. Of the five peptides, $P_2$ exhibited the least H-2 restriction (recognised by H-$2^b$ and H-$2^k$ but not by H-$2^d$) and promoted serovar B EB antibody production. Further evaluation of lipidic amino acid dimer $P_2$ monomer ("P2 dimer") and lipidic amino acid polylysine LCP-$P_2$ was undertaken.

specific determinants as previously identified with rabbit antisera (Zhang et al, Infect. Immun. 58:1450). These observations suggest that P2 peptide is a potential candidate sequence for providing a Th2 cell site and a B cell sites covering B serogroup serovars and that the LCP preparation significantly enhanced immunogenicity of the P2 sequence.

Immunogenicity of a 30-mer Chimeric Peptide: MAbs to a serovar C omp1 VD I sequence are able to bind to native organisms of various trains in the C serogroup and neutralise chlamydial infectivity in an in vitro neutralisation assay. Thus, a 30-mer chimeric peptide incorporating the $P_2$ peptide sequence and a 13 amino acid sequence from BD I of C omp 1 was constructed as an LCP of formula $(H_1)_8Lys_4Lys_2Lys(NHCH\{(CH_2)_{13}CH_3\}CO)_3NH_2$. The 30-mer chimeric peptide designated as H1 (SAETIFDVTTLNPTIAGSDVAGLQNDPTTN) was constructed as both H1 lipidic monomer and LCP-H1, and these were used to immunise various inbred strains of mice.

Both H1 lipidic monomer and LCP-H1 induced peptide reactive and EB reactive antibodies. B10.D2 (H-$2^d$) strain displayed the lowest antibody response to the Hi sequence consistent with the H-$2^d$ haplotype restriction of immune responses to P2 peptide sequence as seen in Table 1. The anti-peptide antibody titers in sera raised with the LCP-H1 are 10–3200 fold higher than those raised with the H1 lipidic monomer. Antisera were able to bind to whole EBs of serovar A, B, and C coated on ELISA plates. All three serovars were equally well recognised by each sera. The anti-EB antibody titers were 20–40 fold lower than the anti-peptide antibody titers.

Immunoblot and Dot Blot Analysis of H-1 Octamer Antibodies: LCP-H1 antibodies were evaluated by reacting antisera from each of five congenic mouse strains with chlamydial omp1 molecules in immunoblot and with native EBs in dot blot. Antisera from four strains bound to omp1 molecules as well as to native EBs from the three tested serovars A, B and C. B10.D2 (H-$2^d$) antiserum failed to bind.

Epitope Specificity of Antisera Raised with LCP-H1: Epitope specificity of LCP-H1 antisera (1:2000 dilution) was mapped by using a set of complete overlapping hexapeptides covering the entire 30-mer chimeric peptide sequence, see Table 3 below. A two space break is introduced between the first 19 and the last 12 hexapeptides.

produced antibody to two consecutive hexapeptides with the species-specific sequence. Variation in antibody recognition of hexapeptides in the B and C serogroup specific determinants was observed. This was greater for the C serogroup than for the B serogroup determinant. B10 (H-$2^b$) and SJL (H-$2^s$) antisera fall into one pattern, recognising two consecutive hexapeptides in the C serogroup sequence (SDVAGL, DVAGLQ); B10.BR (H-$2^k$) antiserum displayed a second pattern by binding to a single hexapeptide (DVAGLQ): a third pattern was observed with the B10.A (H-$2^a$) serum which bound extensively to multiple hexapeptides in the determinant region at variable titers.

Antisera from B10.D2 strain exhibited no binding to any peptide. The three antigenic determinants mapped with LCP-H1 antisera are similar to those mapped with serovar B and C EB antisera (1:200 dilution) (Table 4). The anti-EB antisera used to react with the first 19 hexapeptides were raised with serovar EBs and those used to react with the last 12 hexapeptides were raised with serovar C EBs.

TABLE 4

| Mouse Strain<br>Hexapeptide | B 10(H-$2^b$)<br>OD (405) | B10.A(H-$2^a$)<br>OD (405) | B10.BR(H-$2^k$)<br>OD (405) |
|---|---|---|---|
| IAQPKS | 0 | 0 | 0 |
| AQPKSA | 0 | 0 | 0 |

TABLE 3

| Mouse Strain<br>Hexapeptide | B 10(H-$2^b$)<br>OD (405) | B10.A(H-$2^a$)<br>OD (405) | B10.D2(H-$2^d$)<br>OD (405) | B10.BR(H-$2^k$)<br>OD (405) | SJL(H-$2^a$)<br>OD (405) |
|---|---|---|---|---|---|
| IAQPKS | 0.1 | <0.1 | <0.1 | <0.1 | <0.1 |
| AQPKSA | 0.1 | 0.1 | <0.1 | <0.1 | 0.1 |
| QPKSAE | 0.1 | <0.1 | <0.1 | <0.1 | <0.1 |
| PKSAET | 0.2 | 0.1 | <0.1 | 0.1 | <0.1 |
| KSAETI | 0.4 | 0.1 | <0.1 | <0.1 | 0.6 |
| SAETIF | 1.2 | 0.3 | 0.1 | 0.3 | 0.2 |
| AETIFD | 0.2 | 0.2 | 0.1 | 0.1 | 0.3 |
| ETIFDV | 0.1 | <0.1 | <0.1 | <0.1 | 0.1 |
| TIFDVT | <0.1 | <0.1 | <0.1 | <0.1 | <0.1 |
| IFDVTT | 0.2 | 0.2 | <0.1 | <0.1 | <0.1 |
| FDVTTL | 0.3 | 0.1 | <0.1 | <0.1 | <0.1 |
| DVTTLN | 0.1 | 0.2 | <0.1 | <0.1 | <0.1 |
| VTTLNP | 0.9 | 0.3 | <0.1 | 0.1 | 0.2 |
| TTLNPT | 0.2 | 0.1 | <0.1 | <0.1 | <0.1 |
| TLNPTI | 2.0 | 1.5 | <0.1 | 1.0 | 1.3 |
| LNPTIA | 1.8 | 0.9 | <0.1 | 0.7 | 0.8 |
| NPTIAG | 0.4 | 0.1 | <0.1 | <0.1 | 0.1 |
| PTIAGA | 0.1 | <0.1 | <0.1 | <0.1 | 0.1 |
| TIAGAG | 0.1 | <0.1 | <0.1 | <0.1 | 0.1 |
| SDVAGL | 0.8 | <0.1 | <0.1 | 0.1 | 1.1 |
| DVAGLQ | 0.7 | 0.9 | <0.1 | 0.3 | 1.2 |
| VAGLQN | 0.2 | 0.3 | <0.1 | <0.1 | <0.1 |
| AGLQND | 0.1 | 0.6 | <0.1 | <0.1 | <0.1 |
| GLQNDP | 0.1 | 0.1 | <0.1 | <0.1 | <0.1 |
| LQNDPT | 0.1 | 0.2 | <0.1 | <0.1 | <0.1 |
| QNDPTT | <0.1 | 0.2 | <0.1 | <0.1 | <0.1 |
| NDPTTN | 0.1 | 0.1 | <0.1 | <0.1 | <0.1 |
| DPTTNV | 0.1 | 0.3 | <0.1 | <0.1 | <0.1 |
| PTTNVA | 0.2 | 0.2 | <0.1 | <0.1 | <0.1 |
| TTNVAR | 0.2 | 0.3 | <0.1 | <0.1 | <0.1 |
| TNVARP | 0.1 | <0.1 | <0.1 | <0.1 | <0.1 |

Three antigenic segments were recognised by the four mouse strains. The three antigenic regions represent chlamydial B serogroup, species, and C serogroup specific epitopes respectively. Antibodies binding to the N-terminal serogroup and central species specific antigenic sites were most probably raised by the P2 sequence of the chimeric peptide. Antibodies binding to the C-terminal C serogroup specific antigenic site were likely raised by the 13-mer sequence derived from serovar C omp 1. All four strains consistently TABLE 4-continued

| | | | |
|---|---|---|---|
| QPKSAE | 0 | 0 | 0 |
| PKSAET | 0 | 0 | 0 |
| KSAETI | 0 | 0 | 0 |
| SAETIF | 0.10 | 0.10 | 0 |
| AETIFD | 0.45 | 0.30 | 0.30 |
| ETIFDV | 0.60 | 0.45 | 0.20 |

TABLE 4-continued

| | | | |
|---|---|---|---|
| TIFDVT | 0.25 | 0.05 | 0 |
| IFDVTT | 0.10 | 0.10 | 0 |
| FDVTTL | 0 | 0.10 | 0 |
| DVTTLN | 0 | 0 | 0 |
| VTTLNP | 0 | 0 | 0 |
| TTLNPT | 0 | 0 | 0 |
| TLNPTI | 0 | 0.30 | 0.10 |
| LNPTIA | 0.20 | 0.15 | 0.20 |
| NPTIAG | 0 | 0 | 0.10 |
| PTIAGA | 0 | 0 | 0 |
| TIAGAG | 0 | 0 | 0 |
| SDVAGL | 0.40 | 0.40 | 0.40 |
| DVAGLQ | 0.45 | 0.20 | 0.30 |
| VAGLQN | 0.20 | 0.05 | 0.05 |
| AGLOND | 0.45 | 0.35 | 0.25 |
| GLQNDP | 0.40 | 0.05 | 0.20 |
| LQNDPT | 0.45 | 0.05 | 0.25 |
| QNDPTT | 0.30 | 0 | 0.05 |
| NDPTTN | 0.50 | 0 | 0.05 |
| DPTTNV | 0.20 | 0 | 0.05 |
| PTTNVA | 0 | 0 | 0 |
| TTNVAR | 0 | 0 | 0 |
| TNVARP | 0 | 0 | 0 |

Effect of NAGO and CGA on Immunogenicity of the LCP-H1 in B10 mice: The effect of NAGO adjuvant on the immunogenicity of LCP-H1 in B10 mice was evaluated and compared to CFA (Table 5). Antisera collected after the second or third immunisation displayed significantly higher antibody titers than the primary antibodies (data not shown). LCP-H1 antibodies using NAGO and CFA were compared for ELISA titer (Table 5), pepscan specificity (Table 6) (antisera used at 1:2000 dilution, raised in B10 (H-$2^b$) mice) and in vitro neutralisation (Table 5). As seen in Table 5, NAGO and CFA induced antibodies of comparable ELISA titer. The fine specificity of epitope binding was also comparable to that elicited by LCP-H1 with CFA in B10 (H-$2^b$) mice Table 5.

TABLE 6-continued

| | | |
|---|---|---|
| SAETIF | 0.2 | 1.2 |
| AETIFD | <0.1 | 0.3 |
| ETIFDV | <0.1 | 0.1 |
| TIFDVT | <0.1 | 0.1 |
| IFDVTT | 1.3 | 0.3 |
| FDVTTL | 0.2 | 0.4 |
| DVTTLN | 0.2 | 0.1 |
| VTTLNP | 0.2 | 1.0 |
| TTLNPT | 0 | 0.3 |
| TLNPTI | 1.6 | 2.1 |
| LNPTIA | 2.2 | 1.8 |
| NPTIAG | 0.1 | 0.4 |
| PTIAGA | 0 | 0.1 |
| TIAGAG | <0.1 | 0.1 |
| SDVAGL | 0.2 | 0.8 |
| DVAGLQ | 0.4 | 0.7 |
| VAGLQN | 0.1 | 0.2 |
| AGLOND | <0.1 | 0.1 |
| GLQNDP | 0.1 | 0.1 |
| LQNDPT | 0 | 0.1 |
| QNDPTT | <0.1 | <0.1 |
| NDPTTN | 0 | <0.1 |
| DPTTNV | 0 | 0.1 |
| PTTNVA | 0 | 0.2 |
| TTNVAR | 0 | 0.2 |
| TNVARP | 0 | <0.1 |

In vitro Neutralisation Activity of LCP-H1 Antibodies: The functional activity of LCP-H1 antibodies was determined by an in vitro HAK cell neutralisation assay. LCP-H1 antisera from responder mice immunised with CFA adjuvant had neutralisation activity against the tested three C. trachomatis serovars. The neutralisation titer was low compared to their binding activity to whole EBs in the ELISA assays (approximately 500-fold less).

The above results show that the polymerisation of peptide by incorporation into a LCP structure significantly enhanced immunogenicity (approximately 100-fold) in comparison to monomeric peptide alone. Furthermore, NAGO adjuvant could be substituted for CFA and result in comparable peptide immunogenicity. This is a significant advantage because the intense inflammatory reaction elicited by CFA proscribes its use in humans. Thus, LCP-H1 in NAGO adjuvant is a useful first generation peptide construct for immunogenicity evaluation.

TABLE 5

| Immunogen | Antigen | B10 (H-$2^b$) ELISA[1] | B10 (H-$2^b$) ND50[2] | B10-A (H-$2^a$) ELISA | B10-A (H-$2^a$) ND50 | B10.BR (H-$2^b$) ELISA | B10.BR (H-$2^b$) ND50 | B10.D2 (H-$2^d$) ELISA | B10.D2 (H-$2^d$) ND50 | SJL (H-$2^s$) ELISA | SJL (H-$2^s$) ND50 |
|---|---|---|---|---|---|---|---|---|---|---|---|
| H1 + CPA | H1 | 1:160 | | 1:160 | | 1:320 | | 1:80 | | | |
| | A EB | 1:160 | | 1:160 | | 1:160 | | 1:80 | | | |
| | B EB | 1:80 | | 1:160 | | 1:160 | | 1:80 | | | |
| | C EB | 1:160 | | 1:320 | | 1:320 | | 1:80 | | | |
| LCP-H1 + CFA | LCP-H1 | 1:512,000 | | 1:128,000 | | 1:64,000 | | 1:800 | | 1:1,024,000 | |
| | A EB | 1:25,600 | 1:60 | 1:3,200 | 1:60 | 1:3,200 | 1:48 | <1:100 | | 1:51,200 | 1:79 |
| | B EB | 1:12,800 | 1:78 | 1:3,200 | 1:60 | 1:1,600 | 1:40 | <1:100 | | 1:25,600 | 1:69 |
| | C EB | 1:25,600 | 1:79 | 1:12,800 | 1:69 | 1:1,600 | 1:60 | <1:100 | | 1:25,600 | 1:79 |
| LCP-H1 + NAGO | LCP-H1 | 1:256,000 | | | | | | | | | |
| | A EB | 1:12,800 | 1:81 | | | | | | | | |
| | B EB | 1:12,800 | 1:79 | | | | | | | | |
| | C EB | 1:25,600 | 1:83 | | | | | | | | |

[1]The ELISA titer was expressed as the highest dilution of antisera which gave an OD value 4-fold above background. The titration was carried out twice in duplicate.
[2]The highest dilution of antisera resulting in 50% reduction of infectivity in an in vitro neutralization assay.

TABLE 6

| Adjuvant Hexapeptide | NAGO OD (405) | CFA OD (405) |
|---|---|---|
| IAQPKS | 0 | <0.1 |
| AQPKSA | 0 | 0.1 |
| QPKSAE | 0 | 0.1 |
| PKSAET | <0.1 | 0.2 |
| KSAETI | <0.1 | 0.5 |

EXAMPLE 3

(Peptide)$_8$Lys$_4$Lys$_2$Lys{HNCH(CH$_2$)$_{13}$CH$_3$CO}$_3$NH$_2$

The peptide is an amino acid sequence derived from foot and mouth disease virus (FMDV). The peptide was designated P6 and has a sequence as follows: PLRAVRPALSG-FDGRVGSG.

Immunogenicity of the LCP-P6 construction was assessed as described for the LCP construction in example 2, with the exception that cows were used instead of mice. 100 μg of LCP-P6 was injected into each cow. Results are shown in Table 7 below.

TABLE 7

| Days after inoculation | Neutralising antibody response using serum diluted 1/100 | |
|---|---|---|
| | Virus neutralised log$_{10}$ | |
| | Cow 1 | Cow 2 |
| 35 | 3.0 | 2.5 |
| 55 | 3.0 | 2.3 |
| 110 | 3.0 | 1.5 |
| 133 | 3.0 | 2.0 |

The above results are approximately 10 times higher than would be expected from a conventional KLH or BSA conjugated FMDV.

---

We claim:

1. A peptide compound comprising at least 2 amino acid moieties joined together by peptide bonds, the compound comprising a lipophilic anchor which is connected to an amino acid moiety of the compound by a peptide bond and which comprises at least two amino acid moieties directly joined to one another by peptide bonds, each amino acid moiety being of the formula I

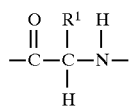

wherein each $R^1$ is independently a linear or branched chain alkyl or alkenyl group having 6–24 carbon atoms, the compound comprising also a matrix core section comprising n levels of dendritically linked trifunctional amino acid moieties, in which n is an integer of 2 or more, the or each trifunctional amino acid moieties comprising either two carboxylic acid groups or two amine groups and the matrix core having at least two terminal functionalities which are selected from —$NH_2$, —COOH, —OH, —SH and derivatives thereof.

2. A peptide compound according to claim 1, wherein n is 2, 3 or 4.

3. A peptide compound according to claim 1 wherein the lipophilic anchor section is joined to the central amino acid of the matrix core section, directly or via a linker group.

4. A compound comprising a peptide compound according to claim 1, in which a pharmaceutically active substituent is joined to each of the terminal functionalities.

5. A compound according to claim 4, wherein all of the pharmaceutically active substituents are the same.

6. A compound according to claim 4, wherein each pharmaceutically active substituent is joined to the peptide compound by a peptide bond.

7. A composition comprising a compound according to claim 4 and a pharmaceutically active carrier.

8. A composition according to claim 7, wherein the compound comprises a peptide antigen capable of eliciting an immune response.

9. A liposome composition comprising a compound according to claim 1 anchored in a lipid vesicle via the lipophilic anchor section.

10. A liposome composition according to claim 9, wherein the compound comprises a peptide antigen capable of eliciting an immune response.

11. A compound according to claim 1 additionally comprising a resin support linked directly via a peptide bond or indirectly via a linker peptide moiety to the lipophilic anchor section.

12. A compound according to claim 1 having the formula

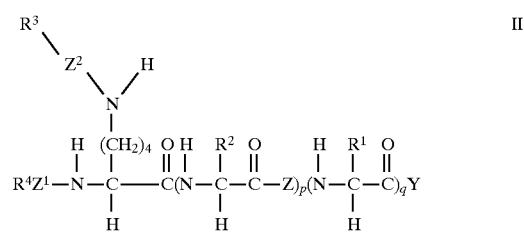

wherein Z, $Z^1$ and $Z^2$ are independently selected from a bond, an amino-acid residue and an oligopeptide residue, $R^3$ and $R^4$ are independently selected from H, an amine protecting group, a pharmaceutically active moiety, and a group III

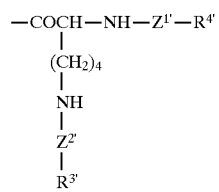

wherein $R^{3'}$, $R^{4'}$, $Z^{1'}$ and $Z^{2'}$ are selected from the same groups represented by $R^3$, $R^{4'}$ $Z^1$ and $Z^2$, respectively, p is 0 or an integer, the or each $R^2$ is independently selected from linear and branched chain alkyl and alkenyl groups having 6 to 24 carbon atoms and naturally-occurring amino acid side chains, q is an integer of at least 1 the or each $R^1$ is independently selected from linear and branched chain alkyl and alkenyl groups having 6 to 24 carbon atoms, Y is OH, $NH_2$, a carboxylic acid protecting group or comprises an amino acid or oligopeptide moiety a resin on which the peptide has been synthesised.

13. A process of producing a peptide compound comprising a lipophilic anchor which is connected to an amino acid moiety of the compound by a peptide bond and which comprises at least two amino acid moieties directly Joined to one another by peptide bonds, each amino acid moiety being of the formula I

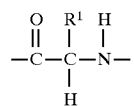

wherein each $R^1$ is independently a linear or branched chain alkyl or alkenyl group having 6–24 carbon atoms, the compound comprising also a matrix core section comprising n levels of dendritically linked trifunctional amino acid moieties, in which n is an integer of 2 or more, the or each trifunctional amino acid moieties comprising either two carboxylic acid groups or two amine groups and the matrix core having at least two terminal functionalities which are selected from $—NH_2$, —COOH, —OH, —SH and derivatives thereof, said process comprising reacting of the amine or carboxylic acid equivalent of the lipophilic anchor with the carboxylic acid or amine equivalent, respectively, of said amino acid moiety of the compound to form said peptide bond.

14. A process according to claim 13, wherein the formation of said peptide compound is carried out as a solid phase peptide synthesis step in which the forming peptide compound is attached to a resin.

15. A process according to claim 14, wherein the process comprises the formation of peptide bonds between the moieties of formula I and of peptide bonds between the amino acid moieties of the matrix core section, sequentially and without cleavage of the forming peptide compound from the resin.

16. A process according to claim 15, wherein the peptide compound is a compound joined to each of the terminal functionalities by a peptide bond and wherein each terminal functionality is amine or carboxylic acid group or derivative thereof and wherein each peptide bond which joins a pharmaceutically active substituent to a terminal functionality is formed by reacting the amine or carboxylic acid moiety or derivative thereof of said pharmaceutically-active substituent with said terminal functionality whilst the forming peptide compound is attached to the resin.

* * * * *

SEQUENCE LISTING ( 1 ) GENERAL INFORMATION:

( i i i ) NUMBER OF SEQUENCES: 39

( 2 ) INFORMATION FOR SEQ ID NO: 1:

( i ) SEQUENCE CHARACTERISTICS:
        ( A ) LENGTH: 61 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: internal ( x i ) SEQUENCE DESCRIPTION: SEQ ID NO: 1:

```
Arg Ala Ser Phe Asp Ala Asp Thr Ile Arg Ile Ala Gln Pro Lys Ser
 1               5                  10                  15

Ala Glu Thr Ile Phe Asp Val Thr Thr Leu Asn Pro Thr Ile Ala Gly
             20                  25                  30

Ala Gly Asp Val Lys Thr Ser Ala Glu Gly Gln Leu Gly Asp Thr Met
         35                  40                  45

Gln Ile Val Ser Leu Gln Leu Asn Lys Met Lys Ser Arg
         50                  55                  60
```

( 2 ) INFORMATION FOR SEQ ID NO: 2:

( i ) SEQUENCE CHARACTERISTICS:
        ( A ) LENGTH: 23 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: internal ( x i ) SEQUENCE DESCRIPTION: SEQ ID NO: 2:

```
Arg Ala Ser Phe Asp Ala Asp Thr Ile Arg Ile Ala Gln Pro Lys Ser
 1               5                  10                  15
```

Ala Glu Thr Ile Phe Asp Gly
                20

(2) INFORMATION FOR SEQ ID NO: 3:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 3:

Ala Glu Thr Ile Phe Asp Val Thr Thr Leu Asn Pro Thr Ile Ala Gly
1               5                   10                  15

(2) INFORMATION FOR SEQ ID NO: 4:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 4:

Thr Thr Leu Asn Pro Thr Ile Ala Gly Ala Gly Asp Val Lys Thr Ser
1               5                   10                  15
Ala Glu Gly (2) INFORMATION FOR SEQ ID NO: 5:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 5:

Lys Thr Ser Ala Glu Gly Gln Leu Gly Asp Thr Met Gln Ile Val Gly
1               5                   10                  15

(2) INFORMATION FOR SEQ ID NO: 6:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 6:

Thr Met Gln Ile Val Ser Leu Gln Leu Asn Lys Met Lys Ser Arg Gly
1               5                   10                  15

(2) INFORMATION FOR SEQ ID NO: 7:

( i ) SEQUENCE CHARACTERISTICS:
 ( A ) LENGTH: 19 amino acids
 ( B ) TYPE: amino acid
 ( C ) STRANDEDNESS:
 ( D ) TOPOLOGY: linear ( i i ) MOLECULE TYPE: peptide ( v ) FRAGMENT TYPE: internal ( x i ) SEQUENCE DESCRIPTION: SEQ ID NO: 7:

```
Pro Leu Arg Ala Val Arg Pro Ala Leu Ser Gly Phe Asp Gly Arg Val
 1               5                  10                  15
Gly Ser Gly
```

( 2 ) INFORMATION FOR SEQ ID NO: 8:

( i ) SEQUENCE CHARACTERISTICS:
 ( A ) LENGTH: 30 amino acids
 ( B ) TYPE: amino acid
 ( C ) STRANDEDNESS:
 ( D ) TOPOLOGY: linear ( i i ) MOLECULE TYPE: peptide ( v ) FRAGMENT TYPE: internal ( x i ) SEQUENCE DESCRIPTION: SEQ ID NO: 8:

```
Ser Ala Glu Thr Ile Phe Asp Val Thr Thr Leu Asn Pro Thr Ile Ala
 1               5                  10                  15
Gly Ser Asp Val Ala Gly Leu Gln Asn Asp Pro Thr Thr Asn
                20                  25                  30
```

( 2 ) INFORMATION FOR SEQ ID NO: 9:

( i ) SEQUENCE CHARACTERISTICS:
 ( A ) LENGTH: 6 amino acids
 ( B ) TYPE: amino acid
 ( C ) STRANDEDNESS:
 ( D ) TOPOLOGY: linear ( i i ) MOLECULE TYPE: peptide ( v ) FRAGMENT TYPE: internal ( x i ) SEQUENCE DESCRIPTION: SEQ ID NO: 9:

```
Ile Ala Gln Pro Lys Ser
 1               5
```

( 2 ) INFORMATION FOR SEQ ID NO: 10:

( i ) SEQUENCE CHARACTERISTICS:
 ( A ) LENGTH: 6 amino acids
 ( B ) TYPE: amino acid
 ( C ) STRANDEDNESS:
 ( D ) TOPOLOGY: linear ( i i ) MOLECULE TYPE: peptide ( v ) FRAGMENT TYPE: internal ( x i ) SEQUENCE DESCRIPTION: SEQ ID NO: 10:

```
Ala Gln Pro Lys Ser Ala
 1               5
```

( 2 ) INFORMATION FOR SEQ ID NO: 11:

( i ) SEQUENCE CHARACTERISTICS:
 ( A ) LENGTH: 6 amino acids (B) TYPE: amino acid
(C) STRANDEDNESS:
(D) TOPOLOGY: linear (ii) MOLECULE TYPE: peptide (v) FRAGMENT TYPE: internal (xi) SEQUENCE DESCRIPTION: SEQ ID NO: 11:

Gln Pro Lys Ser Ala Glu
1               5

(2) INFORMATION FOR SEQ ID NO: 12:

(i) SEQUENCE CHARACTERISTICS:
(A) LENGTH: 6 amino acids
(B) TYPE: amino acid
(C) STRANDEDNESS:
(D) TOPOLOGY: linear (ii) MOLECULE TYPE: peptide (v) FRAGMENT TYPE: internal (xi) SEQUENCE DESCRIPTION: SEQ ID NO: 12:

Pro Lys Ser Ala Glu Thr
1               5

(2) INFORMATION FOR SEQ ID NO: 13:

(i) SEQUENCE CHARACTERISTICS:
(A) LENGTH: 6 amino acids
(B) TYPE: amino acid
(C) STRANDEDNESS:
(D) TOPOLOGY: linear (ii) MOLECULE TYPE: peptide (v) FRAGMENT TYPE: internal (xi) SEQUENCE DESCRIPTION: SEQ ID NO: 13:

Lys Ser Ala Glu Thr Ile
1               5

(2) INFORMATION FOR SEQ ID NO: 14:

(i) SEQUENCE CHARACTERISTICS:
(A) LENGTH: 6 amino acids
(B) TYPE: amino acid
(C) STRANDEDNESS:
(D) TOPOLOGY: linear (ii) MOLECULE TYPE: peptide (v) FRAGMENT TYPE: internal (xi) SEQUENCE DESCRIPTION: SEQ ID NO: 14:

Ser Ala Glu Thr Ile Phe
1               5

(2) INFORMATION FOR SEQ ID NO: 15:

(i) SEQUENCE CHARACTERISTICS:
(A) LENGTH: 6 amino acids
(B) TYPE: amino acid
(C) STRANDEDNESS:
(D) TOPOLOGY: linear (ii) MOLECULE TYPE: peptide (v) FRAGMENT TYPE: internal ( x i ) SEQUENCE DESCRIPTION: SEQ ID NO: 15:

Ala  Glu  Thr  Ile  Phe  Asp
1                    5

( 2 ) INFORMATION FOR SEQ ID NO: 16:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: internal ( x i ) SEQUENCE DESCRIPTION: SEQ ID NO: 16:

Glu  Thr  Ile  Phe  Asp  Val
1                    5

( 2 ) INFORMATION FOR SEQ ID NO: 17:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: internal ( x i ) SEQUENCE DESCRIPTION: SEQ ID NO: 17:

Thr  Ile  Phe  Asp  Val  Thr
1                    5

( 2 ) INFORMATION FOR SEQ ID NO: 18:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: internal ( x i ) SEQUENCE DESCRIPTION: SEQ ID NO: 18:

Ile  Phe  Asp  Val  Thr  Thr
1                    5

( 2 ) INFORMATION FOR SEQ ID NO: 19:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: internal ( x i ) SEQUENCE DESCRIPTION: SEQ ID NO: 19:

Phe  Asp  Val  Thr  Thr  Leu
1                    5

( 2 ) INFORMATION FOR SEQ ID NO: 20:

( i ) SEQUENCE CHARACTERISTICS:
    ( A ) LENGTH: 6 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: internal ( x i ) SEQUENCE DESCRIPTION: SEQ ID NO: 20:

Asp Val Thr Thr Leu Asn
1               5

( 2 ) INFORMATION FOR SEQ ID NO: 21:

( i ) SEQUENCE CHARACTERISTICS:
    ( A ) LENGTH: 6 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: internal ( x i ) SEQUENCE DESCRIPTION: SEQ ID NO: 21:

Val Thr Thr Leu Asn Pro
1               5

( 2 ) INFORMATION FOR SEQ ID NO: 22:

( i ) SEQUENCE CHARACTERISTICS:
    ( A ) LENGTH: 6 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: internal ( x i ) SEQUENCE DESCRIPTION: SEQ ID NO: 22:

Thr Thr Leu Asn Pro Thr
1               5

( 2 ) INFORMATION FOR SEQ ID NO: 23:

( i ) SEQUENCE CHARACTERISTICS:
    ( A ) LENGTH: 6 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: internal ( x i ) SEQUENCE DESCRIPTION: SEQ ID NO: 23:

Thr Leu Asn Pro Thr Ile
1               5

( 2 ) INFORMATION FOR SEQ ID NO: 24:

( i ) SEQUENCE CHARACTERISTICS:
    ( A ) LENGTH: 6 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: internal ( x i ) SEQUENCE DESCRIPTION: SEQ ID NO: 24:

Leu Asn Pro Thr Ile Ala
1               5

( 2 ) INFORMATION FOR SEQ ID NO: 25:

( i ) SEQUENCE CHARACTERISTICS:
    ( A ) LENGTH: 6 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: internal ( x i ) SEQUENCE DESCRIPTION: SEQ ID NO: 25:

Asn Pro Thr Ile Ala Gly
1               5

( 2 ) INFORMATION FOR SEQ ID NO: 26:

( i ) SEQUENCE CHARACTERISTICS:
    ( A ) LENGTH: 6 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: internal ( x i ) SEQUENCE DESCRIPTION: SEQ ID NO: 26:

Pro Thr Ile Ala Gly Ala
1               5

( 2 ) INFORMATION FOR SEQ ID NO: 27:

( i ) SEQUENCE CHARACTERISTICS:
    ( A ) LENGTH: 6 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: internal ( x i ) SEQUENCE DESCRIPTION: SEQ ID NO: 27:

Thr Ile Ala Gly Ala Gly
1               5

( 2 ) INFORMATION FOR SEQ ID NO: 28:

( i ) SEQUENCE CHARACTERISTICS:
    ( A ) LENGTH: 6 amino acids
    ( B ) TYPE: amino acid
    ( C ) STRANDEDNESS:
    ( D ) TOPOLOGY: linear ( i i ) MOLECULE TYPE: peptide ( v ) FRAGMENT TYPE: internal ( x i ) SEQUENCE DESCRIPTION: SEQ ID NO: 28:

Ser Asp Val Ala Gly Leu
1               5

(2) INFORMATION FOR SEQ ID NO: 29:

(i) SEQUENCE CHARACTERISTICS:
(A) LENGTH: 6 amino acids
(B) TYPE: amino acid
(C) STRANDEDNESS:
(D) TOPOLOGY: linear (ii) MOLECULE TYPE: peptide (v) FRAGMENT TYPE: internal (xi) SEQUENCE DESCRIPTION: SEQ ID NO: 29:

Asp Val Ala Gly Leu Gln
1               5

(2) INFORMATION FOR SEQ ID NO: 30:

(i) SEQUENCE CHARACTERISTICS:
(A) LENGTH: 6 amino acids
(B) TYPE: amino acid
(C) STRANDEDNESS:
(D) TOPOLOGY: linear (ii) MOLECULE TYPE: peptide (v) FRAGMENT TYPE: internal (xi) SEQUENCE DESCRIPTION: SEQ ID NO: 30:

Val Ala Gly Leu Gln Asn
1               5

(2) INFORMATION FOR SEQ ID NO: 31:

(i) SEQUENCE CHARACTERISTICS:
(A) LENGTH: 6 amino acids
(B) TYPE: amino acid
(C) STRANDEDNESS:
(D) TOPOLOGY: linear (ii) MOLECULE TYPE: peptide (v) FRAGMENT TYPE: internal (xi) SEQUENCE DESCRIPTION: SEQ ID NO: 31:

Ala Gly Leu Gln Asn Asp
1               5

(2) INFORMATION FOR SEQ ID NO: 32:

(i) SEQUENCE CHARACTERISTICS:
(A) LENGTH: 6 amino acids
(B) TYPE: amino acid
(C) STRANDEDNESS:
(D) TOPOLOGY: linear (ii) MOLECULE TYPE: peptide (v) FRAGMENT TYPE: internal (xi) SEQUENCE DESCRIPTION: SEQ ID NO: 32:

Gly Leu Gln Asn Asp Pro
1               5

(2) INFORMATION FOR SEQ ID NO: 33:

(i) SEQUENCE CHARACTERISTICS:
(A) LENGTH: 6 amino acids
(B) TYPE: amino acid
(C) STRANDEDNESS:
(D) TOPOLOGY: linear -continued (i i) MOLECULE TYPE: peptide (v) FRAGMENT TYPE: internal (x i) SEQUENCE DESCRIPTION: SEQ ID NO: 33:

```
Leu  Gln  Asn  Asp  Pro  Thr
1                     5
```

(2) INFORMATION FOR SEQ ID NO: 34:

(i) SEQUENCE CHARACTERISTICS:
        (A) LENGTH: 6 amino acids
        (B) TYPE: amino acid
        (C) STRANDEDNESS:
        (D) TOPOLOGY: linear (i i) MOLECULE TYPE: peptide (v) FRAGMENT TYPE: internal (x i) SEQUENCE DESCRIPTION: SEQ ID NO: 34:

```
Gln  Asn  Asp  Pro  Thr  Thr
1                     5
```

(2) INFORMATION FOR SEQ ID NO: 35:

(i) SEQUENCE CHARACTERISTICS:
        (A) LENGTH: 6 amino acids
        (B) TYPE: amino acid
        (C) STRANDEDNESS:
        (D) TOPOLOGY: linear (i i) MOLECULE TYPE: peptide (v) FRAGMENT TYPE: internal (x i) SEQUENCE DESCRIPTION: SEQ ID NO: 35:

```
Asn  Asp  Pro  Thr  Thr  Asn
1                     5
```

(2) INFORMATION FOR SEQ ID NO: 36:

(i) SEQUENCE CHARACTERISTICS:
        (A) LENGTH: 6 amino acids
        (B) TYPE: amino acid
        (C) STRANDEDNESS:
        (D) TOPOLOGY: linear (i i) MOLECULE TYPE: peptide (v) FRAGMENT TYPE: internal (x i) SEQUENCE DESCRIPTION: SEQ ID NO: 36:

```
Asp  Pro  Thr  Thr  Asn  Val
1                     5
```

(2) INFORMATION FOR SEQ ID NO: 37:

(i) SEQUENCE CHARACTERISTICS:
        (A) LENGTH: 6 amino acids
        (B) TYPE: amino acid
        (C) STRANDEDNESS:
        (D) TOPOLOGY: linear (i i) MOLECULE TYPE: peptide (v) FRAGMENT TYPE: internal (x i) SEQUENCE DESCRIPTION: SEQ ID NO: 37:

```
Pro  Thr  Thr  Asn  Val  Ala
1                     5
```

(2) INFORMATION FOR SEQ ID NO: 38:

(i) SEQUENCE CHARACTERISTICS:
    (A) LENGTH: 6 amino acids
    (B) TYPE: amino acid
    (C) STRANDEDNESS:
    (D) TOPOLOGY: linear (ii) MOLECULE TYPE: peptide (v) FRAGMENT TYPE: internal (xi) SEQUENCE DESCRIPTION: SEQ ID NO: 38:

Thr  Thr  Asn  Val  Ala  Arg
  1                  5

(2) INFORMATION FOR SEQ ID NO: 39:

(i) SEQUENCE CHARACTERISTICS:
    (A) LENGTH: 6 amino acids
    (B) TYPE: amino acid
    (C) STRANDEDNESS:
    (D) TOPOLOGY: linear (ii) MOLECULE TYPE: peptide (v) FRAGMENT TYPE: internal (xi) SEQUENCE DESCRIPTION: SEQ ID NO: 39:

Thr  Asn  Val  Ala  Arg  Pro
  1                  5